(12) United States Patent
Widger et al.

(10) Patent No.: US 10,150,899 B2
(45) Date of Patent: *Dec. 11, 2018

(54) POLYMER FORMULATIONS FOR USE WITH ELECTRO-OPTIC MEDIA

(71) Applicant: E Ink Corporation, Billerica, MA (US)

(72) Inventors: Peter Carsten Bailey Widger, Nashua, NH (US); Lynne A. McCullough, Medford, MA (US); Russell J. Dewitte, Mendon, MA (US); Richard J. Paolini, Jr., Framingham, MA (US); Thomas Fauvell, Chicago, IL (US); Jonathan Kim Nguyen, Rockland, MA (US); Eugene Bzowej, Reading, MA (US)

(73) Assignee: E Ink Corporation, Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/689,399

(22) Filed: Aug. 29, 2017

(65) Prior Publication Data
US 2017/0362479 A1     Dec. 21, 2017

Related U.S. Application Data

(63) Continuation of application No. 15/217,206, filed on Jul. 22, 2016, now Pat. No. 9,777,201.
(Continued)

(51) Int. Cl.
*C09J 175/06*     (2006.01)
*G01N 23/223*     (2006.01)
(Continued)

(52) U.S. Cl.
CPC .......... *C09J 175/06* (2013.01); *G01N 23/223* (2013.01); *G02F 1/15* (2013.01); *G02F 1/167* (2013.01); *G01N 2223/633* (2013.01); *G02F 2001/133357* (2013.01); *G02F 2202/28* (2013.01)

(58) Field of Classification Search
CPC ................. C09J 175/06; G01N 23/223; G01N 2223/633; G02F 1/167; G02F 1/15; G02F 2001/133357; G02F 2202/28
See application file for complete search history.

(56) References Cited

U.S. PATENT DOCUMENTS 4,418,346 A     11/1983     Batchelder
5,760,761 A     6/1998     Sheridon
(Continued)

OTHER PUBLICATIONS

Wood, D., "An Electrochromic Renaissance?" Information Display, 18(3), 24 (Mar. 2002) Mar. 1, 2002.
(Continued)

*Primary Examiner* — Bijan Ahvazi
(74) *Attorney, Agent, or Firm* — Brian D. Bean

(57) ABSTRACT

Polymer formulations including urethane acrylates, adhesion promoters, and conductive monomers. By selecting suitable conductive monomers, it is possible to achieve formulations having a volume resistivity from $10^6$ to $10^{10}$ Ohm·cm after being conditioned for one week at 25° C. and 50% relative humidity. Such formulations are suitable for incorporation into electro-optic materials, such as electro-optic displays or variable transmission films, e.g., for architectural applications. In other embodiments, the formulations additionally include metal oxide nanoparticles to alter the refractive index and/or conductivity.

16 Claims, 14 Drawing Sheets

Related U.S. Application Data

(60) Provisional application No. 62/195,943, filed on Jul. 23, 2015.

(51) Int. Cl.
  *G02F 1/167* (2006.01)
  *G02F 1/15* (2006.01)
  *G02F 1/1333* (2006.01)

(56) References Cited

U.S. PATENT DOCUMENTS

| | | | |
|---|---|---|---|
| 5,777,782 | A | 7/1998 | Sheridon |
| 5,808,783 | A | 9/1998 | Crowley |
| 5,821,001 | A | 10/1998 | Arbab |
| 5,872,552 | A | 2/1999 | Gordon, II |
| 6,054,071 | A | 4/2000 | Mikkelsen, Jr. |
| 6,055,091 | A | 4/2000 | Sheridon |
| 6,097,531 | A | 8/2000 | Sheridon |
| 6,128,124 | A | 10/2000 | Silverman |
| 6,130,774 | A | 10/2000 | Albert |
| 6,137,467 | A | 10/2000 | Sheridon |
| 6,144,361 | A | 11/2000 | Gordon, II |
| 6,147,791 | A | 11/2000 | Sheridon |
| 6,172,798 | B1 | 1/2001 | Albert |
| 6,184,856 | B1 | 2/2001 | Gordon, II |
| 6,225,971 | B1 | 5/2001 | Gordon, II |
| 6,241,921 | B1 | 6/2001 | Jacobson |
| 6,271,823 | B1 | 8/2001 | Gordon, II |
| 6,301,038 | B1 | 10/2001 | Fitzmaurice |
| 6,672,921 | B1 | 1/2004 | Liang |
| 6,866,760 | B2 | 3/2005 | Paolini, Jr. |
| 6,870,657 | B1 | 3/2005 | Fitzmaurice |
| 6,922,276 | B2 | 7/2005 | Zhang et al. |
| 6,942,824 | B1 | 9/2005 | Li |
| 6,950,220 | B2 | 9/2005 | Abramson et al. |
| 6,982,178 | B2 | 1/2006 | LeCain et al. |
| 7,002,728 | B2 | 2/2006 | Pullen et al. |
| 7,012,735 | B2 | 3/2006 | Honeyman et al. |
| 7,075,502 | B1 | 7/2006 | Drzaic |
| 7,110,163 | B2 | 9/2006 | Webber et al. |
| 7,116,318 | B2 | 10/2006 | Amundson et al. |
| 7,173,752 | B2 | 2/2007 | Doshi et al. |
| 7,236,291 | B2 | 6/2007 | Kaga et al. |
| 7,312,784 | B2 | 12/2007 | Baucom et al. |
| 7,321,459 | B2 | 1/2008 | Masuda et al. |
| 7,339,715 | B2 | 3/2008 | Webber et al. |
| 7,342,068 | B2 | 3/2008 | Klingenberg |
| 7,411,719 | B2 | 8/2008 | Paolini, Jr. et al. |
| 7,420,549 | B2 | 9/2008 | Jacobson |
| 7,535,624 | B2 | 5/2009 | Amundson et al. |
| 7,561,324 | B2 | 7/2009 | Duthaler et al. |
| 7,679,814 | B2 | 3/2010 | Paolini, Jr. et al. |
| 7,839,564 | B2 | 11/2010 | Whitesides et al. |
| 8,009,348 | B2 | 8/2011 | Zehner |
| 8,188,942 | B2 | 5/2012 | Yoo |
| 8,319,759 | B2 | 11/2012 | Jacobson |
| 8,531,757 | B2 | 9/2013 | Moriyama |
| 9,152,004 | B2 | 10/2015 | Paolini, Jr. |
| 2004/0085619 | A1 | 5/2004 | Wu |
| 2012/0258305 | A1 | 10/2012 | Haruta |
| 2015/0226986 | A1 | 8/2015 | Paolini, Jr. |

OTHER PUBLICATIONS

O'Regan, B. et al., "A Low Cost, High-efficiency Solar Cell Based on Dye-sensitized colloidal TiO2 Films", Nature, vol. 353, pp. 737-740 (Oct. 24, 1991). Oct. 24, 1991.

Bach, U. et al., "Nanomaterials-Based Electrochromics for Paper-Quality Displays", Adv. Mater, vol. 14, No. 11, pp. 845-848 (Jun. 2002). Jun. 5, 2002.

Hayes, R.A. et al., "Video-Speed Electronic Paper Based on Electrowetting", Nature, vol. 425, No. 25, pp. 383-385 (Sep. 2003). Sep. 25, 2003.

Kitamura, T. et al., "Electrical toner movement for electronic paper-like display", Asia Display/IDW '01, pp. 1517-1520, Paper HCS1-1 (2001). Jan. 1, 2001.

Yamaguchi, Y. et al., "Toner display using insulative particles charged triboelectrically", Asia Display/IDW '01, pp. 1729-1730, Paper AMD4-4 (2001). Jan. 1, 2001.

Korean Intellectual Property Office; PCT/US2016/043563; International Search Report and Written Opinion; dated Oct. 21, 2016. dated Oct. 21, 2016.

| Electrode |
|---|
| E-O Medium |
| Planarization Layer |
| Electrode |
| Adhesive |
| Reflective Substrate |

FIG. 11A

| Electrode |
|---|
| Planarization Layer |
| E-O Medium |
| Electrode |
| Adhesive |
| Reflective Substrate |

FIG. 11B

POLYMER FORMULATIONS FOR USE WITH ELECTRO-OPTIC MEDIA

REFERENCE TO RELATED APPLICATIONS

This application is a continuation of U.S. patent application Ser. No. 15/217,206, filed Jul. 22, 2016, now U.S. Pat. No. 9,777,201, which claims priority to U.S. Provisional Application No. 62/195,943, filed Jul. 23, 2015, both of which are incorporated herein by reference in its entirety.

BACKGROUND OF INVENTION

The invention relates to polymer formulations for use in the fabrication of electro-optic devices. Such devices can include a variety of electro-optic media, including electrophoretic media, electrochromic media, light-emitting diode media, or liquid crystal media. In particular, the invention is useful for improving the performance of layered assemblies including electro-optic media that are incorporated into electro-optic displays, such as displays found in monitors, mobile devices, tablets, electronic readers, and signs. The invention is also useful for fabricating bulk materials having electrically-switchable optical characteristics, such as variable transmission media, which may be incorporated into windows, art, furniture, or other architectural products.

A front plane laminate (FPL) e.g., as described in U.S. Pat. No. 6,982,178, typically consists of at least a transparent electrode, an electro-optic medium, an adhesive layer and a release layer. Assembly of an electro-optic display using an FPL may be effected by removing the release sheet from the FPL and contacting the adhesive layer with a backplane under conditions effective to cause the adhesive layer to adhere to the backplane, thereby securing the adhesive layer, layer of electro-optic medium and electrically-conductive layer to the backplane. See FIG. 1A. This process is well-adapted to mass production since the front plane laminate may be mass produced, typically using roll-to-roll coating techniques, and then cut into pieces of any size needed for use with specific backplanes. In some embodiments, the backplane is microfabricated to include an active matrix of transistors.

As an alternative to a "simple" FPL, as described above, U.S. Pat. No. 7,561,324 describes a so-called "double release sheet" which is essentially a simplified version of the front plane laminate of U.S. Pat. No. 6,982,178. One form of the double release sheet comprises a layer of a solid electro-optic medium sandwiched between two adhesive layers, one or both of the adhesive layers being covered by a release sheet. Another form of the double release sheet comprises a layer of a solid electro-optic medium sandwiched between two release sheets. Both forms of the double release film are intended for use in a process generally similar to the process for assembling an electro-optic display from a front plane laminate (FPL) already described, but involving two separate laminations; typically, in a first lamination the double release sheet is laminated to a front electrode to form a front sub-assembly, and then in a second lamination the front sub-assembly is laminated to a backplane to form the final display, although the order of these two laminations could be reversed if desired (See FIG. 1C).

As an alternative construction, U.S. Pat. No. 7,839,564 describes a so-called "inverted front plane laminate", which is a variant of the front plane laminate described in U.S. Pat. No. 6,982,178. This inverted front plane laminate comprises, in order, at least one of a light-transmissive protective layer and a light-transmissive electrically-conductive layer; an adhesive layer; a layer of a solid electro-optic medium; and a release sheet. See FIG. 1B. This inverted front plane laminate is used to form an electro-optic display having a layer of lamination adhesive between the electro-optic layer and the front electrode or front substrate; a second, typically thin layer of adhesive may or may not be present between the electro-optic layer and a backplane. Such electro-optic displays can combine good resolution with good low temperature performance. (See FIG. 1B.)

As discussed in U.S. Pat. Nos. 7,012,735 and 7,173,752, the selection of a lamination adhesive for use in an electro-optic display (or in a front plane laminate, inverted front plane laminate, double release film or other sub-assembly used to produce such an electro-optic display) presents certain problems. Because the lamination adhesive is normally located between the electrodes, which apply the electric field needed to change the electrical state of the electro-optic medium, the conductive properties of the adhesive can influence performance greatly.

For the most part, the volume resistivity of the lamination adhesive controls the overall voltage drop across the electro-optic medium, which is critical factor in the performance of the medium. [The voltage drop across the electro-optic medium is equal to the voltage drop across the electrodes, minus the voltage drop across the lamination adhesive.] On one hand, if the resistivity of the adhesive layer is too high, a substantial voltage drop will occur within the adhesive layer, requiring higher voltages between the electrodes to produce a working voltage drop at the electro-optic medium. Increasing the voltage across the electrodes in this manner is undesirable, however, because it increases power consumption, and may require the use of more complex and expensive control circuitry to produce and switch the increased voltages. On the other hand, if the resistivity of the adhesive layer is too low, there will be undesirable cross-talk between adjacent electrodes (i.e., active matrix electrodes) or the device may simply short out. Also, because the volume resistivity of most materials decreases rapidly with increasing temperature, if the volume resistivity of the adhesive is too low, the performance of the display will vary greatly with temperatures substantially above room temperature.

For these reasons, there is an optimum range of lamination adhesive resistivity values for use with most electro-optic media, this range varying with the resistivity of the electro-optic medium. The volume resistivities of encapsulated electrophoretic media are typically around $10^{10}$ Ohm cm, and the resistivities of other electro-optic media are usually of the same order of magnitude. Accordingly, the volume resistivity of the lamination adhesive should normally be around $10^8$ to $10^{12}$ Ohm cm, or about $10^9$ to $10^{11}$ Ohm cm, assuming an operating temperature of the display, typically around 20° C. Preferably, the lamination adhesive will also have a variation of volume resistivity with temperature that is similar to the electro-optic medium itself.

In addition to the electrical properties, the lamination adhesive must fulfill several mechanical and rheological criteria, including strength of adhesive, flexibility, ability to withstand and flow at lamination temperatures, etc. The number of commercially-available adhesives which can meet all the relevant electrical and mechanical criteria is small, and in practice, the most suitable lamination adhesives are certain polyurethanes, such as those described in U.S. Pat. No. 7,342,068.

To improve the performance of commercially-available polyurethanes, the polyurethanes can be doped with salts or other materials, e.g., as described in the aforementioned U.S. Pat. Nos. 7,012,735 and 7,173,752. A preferred dopant for this purpose is tetrabutylammonium hexafluorophosphate. With experience, it was discovered that adhesives formulated with such dopants damage active matrix backplanes, especially those including transistors made from organic semiconductors. U.S. Pat. No. 8,188,942 showed that, in some embodiments, the salt dopants could be replaced with polymer additives having hydroxyl groups (such as poly (ethylene glycol) to improve the volume resistivity of the adhesive formulations.

Unfortunately, polyurethane compositions with salt and/or polymeric additives have been found to form voids when applied to electro-optic media having irregular surfaces. To counteract the voids, thicker layers of adhesive are applied during the construction of an electro-optic assembly, e.g., a front plane laminate or display. The thicker layers discourage void formation and improve planarity between the electro-optic media and the electrodes. The improved planarity results in more consistent grayscales over the surface of a display, however, the increased thickness reduce sharpness in the display because the field lines between the backplane and front electrode are more diffuse. Copending application Ser. No. 14/692,854, filed Apr. 22, 2015, describes further efforts to improve the planarity of the adhesive layer while diminishing void formation. Copending application Ser. No. 14/692,854 also discloses substantially solvent-free polyurethane formulations that can be used to produce adhesive layers with improved hardness and durability.

SUMMARY OF INVENTION

The formulations of the invention, i.e., as described herein, overcome the shortcomings of the prior art by providing adhesive and/or planarizing layers with improved conductivity, adhesion, and optical characteristics. The formulations are well-suited for use with a variety of electro-optic media.

In one aspect, this invention provides a polymer composition comprising a urethane acrylate, an adhesion promoter, and a conductive monomer. The composition will typically produce a volume resistivity from $10^6$ to $10^{10}$ Ohm·cm after being conditioned for one week at 25° C. and 50% relative humidity. Typically, the formulation includes very little or substantially no solvent. The polymer composition can be used for a variety of applications where a low-solvent, specific conductivity coating is beneficial, such as in the construction of an electro-optic display. The polymer composition may also include metal oxide particles, e.g., metal oxide nanoparticles. The metal oxide nanoparticles can be selected to alter the index of refraction of the composition so that the overall index of refraction of a layered active material, e.g., a front plane laminate (FPL), matches the index of refraction of the substrate upon which the FPL is placed. For example, the index of refraction of the composition can be engineered to be between 1.0 and 2.0 for visible light.

The polymer composition may additionally include photoinitiators to facilitate UV curing, and/or cross-linkers to improve strength. The polymer composition may also include ionic liquids, such as 1-ethyl-3-methylimidazolium bis[(trifluoromethyl)sulfonyl]imide (EMI TFSI). Exemplary urethane acrylates may include aliphatic and/or aromatic functional groups. Exemplary conductive monomers include functionalized acrylate monomers (and/or oligomers), such as alkoxylated acrylates, caprolactone acrylates, and acrylics. As described herein, the polymer compositions can be tuned to achieve specific conductive, optical, and/or mechanical properties. For example, a non-conductive diluting monomer can be added to achieve a specific volume resistivity for the composition.

The performance of the disclosed polymer formulations can be modified by varying the relative compositions of certain additives, as discussed below. Accordingly, it is possible to produce polymer formulations with specific ranges of volume resistivity, e.g., $10^6$ to $10^{10}$ Ohm·cm after being conditioned for one week at 25° C. and 50% relative humidity, e.g., $10^7$ to $10^9$ Ohm·cm after being conditioned for one week at 25° C. and 50% relative humidity, e.g., $10^8$ to $10^9$ Ohm·cm after being conditioned for one week at 25° C. and 50% relative humidity. In some embodiments, the polymer compositions have a glass transition temperature ($T_g$) of less than −25° C. In some embodiments, the index of refraction of the composition is between 1.0 and 2.0 for visible light, e.g., between 1.2 and 1.7. Furthermore, by varying the composition of the formulations, it is possible to create adhesives for particular use, such as pressure sensitive adhesives.

The polymer compositions of the invention can be used to planarize (make smooth) surfaces with undesired surface morphology, while leaving the surface prepared for bonding or laminating with another structure. For example, the compositions can be spread over an irregular surface and cured to create an adhesive layer that is thin, smooth, and with substantially no voids left between the irregular surface and the composition. While any number of irregular surfaces can be smoothed with the described formulations, the formulations are well suited for the fabrication of microelectronics where there is a need for careful control of the thickness and resistivity of intervening adhesive layers. As described herein, the formulations can be distributed over a surface with spraying, spreading, laminating, pouring, or spin coating. Once applied, the composition can be cured, e.g., by applying heat or by activating with light, e.g., UV light. In some embodiments, the planarized layer may be less than 25 µm thick, i.e., less than 10 µm thick, i.e., less than 5 µm thick, i.e., less than 3 µm thick. The planarized layer may have an overall volume resistivity of less than $10^{10}$ Ohm·cm, i.e., about $10^9$ Ohm·cm.

In another aspect, the polymer compositions of the invention can be incorporated into an electro-optic display. Such displays include an electro-optic medium, a conductive layer, and a polymer composition of the invention (i.e., a urethane acrylate, an adhesion promoter, and a conductive monomer). The electro-optic medium may include liquid crystals, electrochromic materials, or electrophoretic materials. In particular, electro-optic displays using encapsulated electrophoretic media (EEM) are improved with the use of the polymer compositions of the invention as a planarizing adhesive. Typically, during fabrication of a display using EEMs, the EEM layer is spread over a sheet of release or conductive material and dried or cured. Once spread, the layer of EEMs presents an irregular surface morphology that is not well-suited for bonding with another layer of release or electrode. The polymer composition of the invention can be used to smooth out the roughness of the surface of the EEM layer and to prepare the EEM layer to be bound to another substrate or electrode. Furthermore, because the volume resistivity of the polymer composition can be adjusted, the resistivity between electrodes can be modified for optimal performance under target working conditions.

In an embodiment, an electro-optic display may be fabricated by providing an electro-optic medium and contacting the electro-optic medium with a polymer composition of the invention, i.e., comprising a urethane acrylate, an adhesion promoter, and a conductive monomer having a volume resistivity from $10^7$ to $10^{10}$ Ohm·cm. In some instances the electro-optic medium will have surface irregularities that are smoothed over (planarized) by the polymer composition of the invention. The fabrication methods may additionally include curing the polymer composition, e.g., using heat or UV light. Additional steps may include laminating a release sheet or a conductive layer to the polymer composition. This invention also extends to a front plane laminate, inverted front plane laminate or double release sheet incorporating a polymer composition of the invention.

In another aspect, the polymer compositions can be incorporated into a variable transmission (VT) medium whose optical transmission can be modified on demand. Typically, the VT medium will include a transparent substrate, an electro-optic medium, a first transparent electrode, a second transparent electrode, and a polymer composition of the invention (i.e., a urethane acrylate adhesion promoter, a difunctional crosslinker, a nonconductive diluent, and a conductive monomer producing a homopolymer having a volume resistivity from $10^7$ to $10^{10}$ Ohm·cm when cured). Upon application of an electrical signal, the electro-optic medium will change state, resulting in a change in the index of refraction of the VT medium. Depending upon the requirements of the user, the VT medium may change from transparent to translucent, transparent to frosted, or transparent to opaque. Additional components may include color pigments or filters, thus allowing a change in both color and optical transmission. The VT medium can be used for variable transmission windows such as installed in the interior or exterior of a building. Alternatively, the VT medium may be a sign or an optical filter.

Compositions of the invention including nanoparticles, e.g., metal oxide nanoparticles, lend themselves to evaluation with X-ray fluorescence (XRF) spectroscopy. It is determined that XRF intensity for compositions of the invention including certain nanoparticles, such as zirconia, have a roughly linear correlation with thickness of a layer including the formulation. This allows laminate constructs, e.g., front plane laminates (FPL) to be non-destructively evaluated for thickness and regularity during or after fabrication.

By modifying the amount and type of conductive monomer and/or nanoparticle additives, it is possible to achieve an adhesive with a specific index of refraction, thereby allowing the use of a variety of electro-optic media and substrates depending upon the needs of the application. In an embodiment, the electro-optic medium may comprise a polymer-dispersed electrophoretic medium or an encapsulated electrophoretic medium. In some embodiments, the polymer composition will additionally include an ionic liquid, e.g., at a low concentrations.

BRIEF DESCRIPTION OF DRAWINGS

FIG. 11A shows a cross-section through a variable reflective device using a formulation of the invention as a planarization layer/adhesive.

FIG. 11B shows a cross-section through a variable reflective device using a formulation of the invention as a planarization layer/adhesive.

DETAILED DESCRIPTION

Figure 1A:
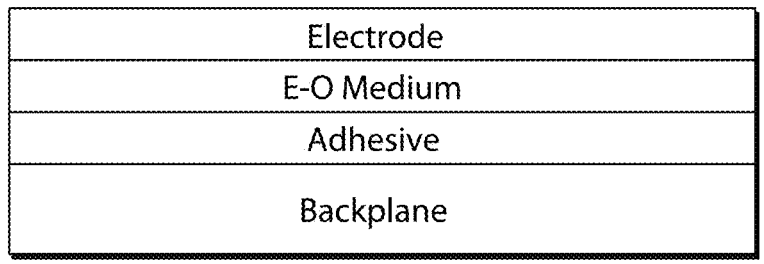
FIG. 1A illustrates a cross-section of an electro-optic display produced using a front plane laminate and a conventional adhesive.
Figure 1B:
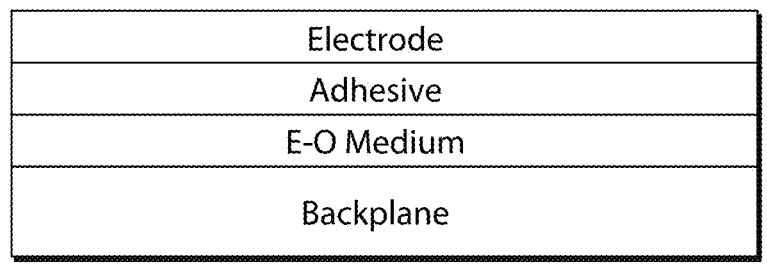
FIG. 1B illustrates a cross-section of an electro-optic display which may be produced using an inverted front plane laminate and a conventional adhesive.
Figure 1C:
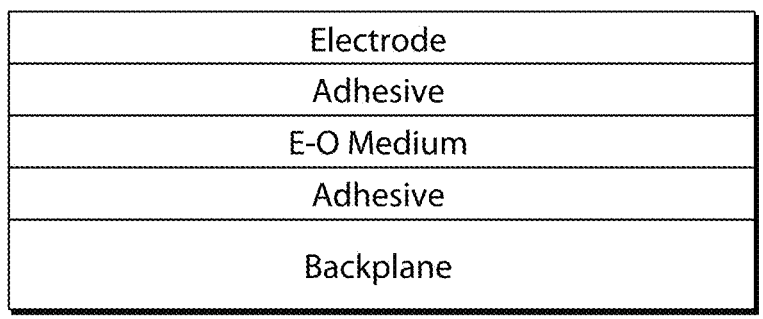
FIG. 1C illustrates a cross-section of an electro-optic display produced using a double release sheet and a conventional adhesive.

As indicated above, the present invention provides polymer formulations for use with a variety of electro-optic media. The polymer formulations improve the performance of devices including electro-optic media because they allow certain adhesive layers to have conductivity, mechanical adhesion, and indexes of refraction that match the electro-optic media and the operating conditions. The polymer formulations also improve performance by allowing for thinner, and more planar, layers of electro-optic media between electrodes, e.g., between a front electrode and a backplane, or between two transparent electrodes.

Polymer formulations of the invention are designed for use in variable transmission (VT) media, such as electro-optic displays, signs, and architectural applications. In order to work with the electro-optic media, the formulations must meet three requirements: they must provide a relatively matched refractive index, they must provide good adhesion between the different layers, (e.g., between ITO and the electro-optic medium), and they must provide appropriate volume resistivity to achieve precise optical state switching. However, each of these values (index of refraction, adhesive strength, and optimum conductivity) can vary greatly depending upon the nature of the electro-optic medium, the application, and the operating conditions.

The term "electro-optic", as applied to a material or a display, is used herein in its conventional meaning in the imaging art to refer to a material having first and second display states differing in at least one optical property, the material being changed from its first to its second display state by application of an electric field to the material. Although the optical property is typically color perceptible to the human eye, it may be another optical property, such as optical transmission, reflectance, and luminescence or, in the case of displays intended for machine reading, pseudo-color in the sense of a change in reflectance of electromagnetic wavelengths outside the visible range.

The term "gray state" is used herein in its conventional meaning in the imaging art to refer to a state intermediate two extreme optical states of a pixel, and does not necessarily imply a black-white transition between these two extreme states. For example, several of the E Ink patents and published applications referred to herein describe electrophoretic displays (EPIDs) in which the extreme states are white and deep blue, so that an intermediate "gray state" would actually be pale blue. Indeed, as already mentioned, the change in optical state may not be a color change at all. The terms "black" and "white" may be used hereinafter to refer to the two extreme optical states of a display, and should be understood as normally including extreme optical states which are not strictly black and white, for example the aforementioned white and dark blue states. The term "monochrome" may be used hereinafter to denote a drive scheme which only drives pixels to their two extreme optical states with no intervening gray states.

The terms "bistable" and "bistability" are used herein in their conventional meaning in the art to refer to displays comprising display elements having first and second display states differing in at least one optical property, and such that after any given element has been driven, by means of an addressing pulse of finite duration, to assume either its first or second display state, after the addressing pulse has terminated, that state will persist for at least several times, for example at least four times, the minimum duration of the addressing pulse required to change the state of the display element. It is shown in U.S. Pat. No. 7,170,670 that some particle-based electrophoretic displays capable of gray scale are stable not only in their extreme black and white states but also in their intermediate gray states, and the same is true of some other types of electro-optic displays. This type of display is properly called "multi-stable" rather than bistable, although for convenience the term "bistable" may be used herein to cover both bistable and multi-stable displays.

Several types of electro-optic displays are known. One type of electro-optic display is a rotating bichromal member type as described, for example, in U.S. Pat. Nos. 5,808,783; 5,777,782; 5,760,761; 6,054,071 6,055,091; 6,097,531; 6,128,124; 6,137,467; and 6,147,791 (although this type of display is often referred to as a "rotating bichromal ball" display, the term "rotating bichromal member" is preferred as more accurate since in some of the patents mentioned above the rotating members are not spherical). Such a display uses a large number of small bodies (typically spherical or cylindrical) which have two or more sections with differing optical characteristics, and an internal dipole. These bodies are suspended within liquid-filled vacuoles within a matrix, the vacuoles being filled with liquid so that the bodies are free to rotate. The appearance of the display is changed by applying an electric field thereto, thus rotating the bodies to various positions and varying which of the sections of the bodies is seen through a viewing surface. This type of electro-optic medium is typically bistable.

Another type of electro-optic display uses an electrochromic medium, for example an electrochromic medium in the form of a nanochromic film comprising an electrode formed at least in part from a semi-conducting metal oxide and a plurality of dye molecules capable of reversible color change attached to the electrode; see, for example O'Regan, B., et al., *Nature* 1991, 353, 737; and Wood, D., *Information Display*, 18(3), 24 (March 2002). See also Bach, U., et al., *Adv. Mater.*, 2002, 14(11), 845. Nanochromic films of this type are also described, for example, in U.S. Pat. Nos. 6,301,038; 6,870,657; and 6,950,220. This type of medium is also typically bistable.

Another type of electro-optic display is an electro-wetting display developed by Philips and described in Hayes, R. A., et al., "Video-Speed Electronic Paper Based on Electrowetting", *Nature*, 425, 383-385 (2003). It is shown in U.S. Pat. No. 7,420,549 that such electro-wetting displays can be made bistable.

One type of electro-optic display, which has been the subject of intense research and development for a number of years, is the particle-based electrophoretic display, in which a plurality of charged particles moves through a fluid under the influence of an electric field. Electrophoretic displays can have attributes of good brightness and contrast, wide viewing angles, state bistability, and low power consumption when compared with liquid crystal displays. Nevertheless, problems with the long-term image quality of these displays have prevented their widespread usage. For example, particles that make up electrophoretic displays tend to settle, resulting in inadequate service-life for these displays.

As noted above, electrophoretic media require the presence of a fluid. In most prior art electrophoretic media, this fluid is a liquid, but electrophoretic media can be produced using gaseous fluids; see, for example, Kitamura, T., et al., "Electrical toner movement for electronic paper-like display", IDW Japan, 2001, Paper HCS1-1, and Yamaguchi, Y., et al., "Toner display using insulative particles charged triboelectrically", IDW Japan, 2001, Paper AMD4-4). See also U.S. Pat. Nos. 7,321,459 and 7,236,291. Such gas-based electrophoretic media appear to be susceptible to the same types of problems due to particle settling as liquid-based electrophoretic media, when the media are used in an orientation which permits such settling, for example in a sign where the medium is disposed in a vertical plane. Indeed, particle settling appears to be a more serious problem in gas-based electrophoretic media than in liquid-based ones, since the lower viscosity of gaseous suspending fluids as compared with liquid ones allows more rapid settling of the electrophoretic particles.

Numerous patents and applications assigned to or in the names of the Massachusetts Institute of Technology (MIT) and E Ink Corporation describe various technologies used in encapsulated electrophoretic and other electro-optic media. Such encapsulated media comprise numerous small capsules, each of which itself comprises an internal phase containing electrophoretically-mobile particles in a fluid medium, and a capsule wall surrounding the internal phase. Typically, the capsules are themselves held within a polymeric binder to form a coherent layer positioned between two electrodes. The technologies described in the these patents and applications include:

(a) Electrophoretic particles, fluids and fluid additives; see for example U.S. Pat. Nos. 7,002,728; and 7,679,814;
(b) Capsules, binders and encapsulation processes; see for example U.S. Pat. Nos. 6,922,276; and 7,411,719;
(c) Films and sub-assemblies containing electro-optic materials; see for example U.S. Pat. Nos. 6,982,178; and 7,839,564;
(d) Backplanes, adhesive layers and other auxiliary layers and methods used in displays; see for example U.S. Pat. Nos. 7,116,318; and 7,535,624;
(e) Color formation and color adjustment; see for example U.S. Pat. No. 7,075,502; and U.S. Patent Application Publication No. 2007/0109219;
(f) Applications of displays; see for example U.S. Pat. No. 7,312,784; and U.S. Patent Application Publication No. 2006/0279527; and
(g) Non-electrophoretic displays, as described in U.S. Pat. Nos. 6,241,921; 6,950,220; and 7,420,549; and U.S. Patent Application Publication No. 2009/0046082.

Many of the aforementioned patents and applications recognize that the walls surrounding the discrete microcapsules in an encapsulated electrophoretic medium could be replaced by a continuous phase, thus producing a so-called polymer-dispersed electrophoretic display (PDEPID), in which the electrophoretic medium comprises a plurality of discrete droplets of an electrophoretic fluid and a continuous phase of a polymeric material, and that the discrete droplets of electrophoretic fluid within such a polymer-dispersed electrophoretic display may be regarded as capsules or microcapsules even though no discrete capsule membrane is associated with each individual droplet; see for example, the aforementioned U.S. Pat. No. 6,866,760. Accordingly, for purposes of the present application, such polymer-dispersed electrophoretic media are regarded as sub-species of encapsulated electrophoretic media.

A related type of electrophoretic display is a so-called "macrocell electrophoretic display". In a macrocell electrophoretic display, the charged particles and the fluid are not encapsulated within microcapsules but instead are retained within a plurality of cavities formed within a carrier medium, typically a polymeric film. See, for example, U.S. Pat. Nos. 6,672,921 and 6,788,449, both assigned to Sipix Imaging, Inc.

Although electrophoretic media are often opaque (since, for example, in many electrophoretic media, the particles substantially block transmission of visible light through the display) and operate in a reflective mode, many electrophoretic displays can be made to operate in a so-called "shutter mode" in which one display state is substantially opaque and one is light-transmissive. See, for example, U.S. Pat. Nos. 5,872,552; 6,130,774; 6,144,361; 6,172,798; 6,271,823; 6,225,971; and 6,184,856. Dielectrophoretic displays, which are similar to electrophoretic displays but rely upon variations in electric field strength, can operate in a similar mode; see U.S. Pat. No. 4,418,346. Other types of electro-optic displays may also be capable of operating in shutter mode. Electro-optic media operating in shutter mode may be useful in multi-layer structures for full color displays; in such structures, at least one layer adjacent the viewing surface of the display operates in shutter mode to expose or conceal a second layer more distant from the viewing surface.

An encapsulated electrophoretic display typically does not suffer from the clustering and settling failure mode of traditional electrophoretic devices and provides further advantages, such as the ability to print or coat the display on a wide variety of flexible and rigid substrates. (Use of the word "printing" is intended to include all forms of printing and coating, including, but without limitation: pre-metered coatings such as patch die coating, slot or extrusion coating, slide or cascade coating, curtain coating; roll coating such as knife over roll coating, forward and reverse roll coating; gravure coating; dip coating; spray coating; meniscus coating; spin coating; brush coating; air knife coating; silk screen printing processes; electrostatic printing processes; thermal printing processes; ink jet printing processes; electrophoretic deposition (See U.S. Pat. No. 7,339,715); and other similar techniques.) Thus, the resulting display can be flexible. Further, because the display medium can be printed (using a variety of methods), the display itself can be made inexpensively.

Other types of electro-optic media may also be used in the displays of the present invention. The bistable or multi-stable behavior of particle-based electrophoretic displays, and other electro-optic displays displaying similar behavior (such displays may hereinafter for convenience be referred to as "impulse driven displays"), is in marked contrast to that of conventional liquid crystal ("LC") displays. Twisted nematic liquid crystals are not bi- or multi-stable but act as voltage transducers, so that applying a given electric field to a pixel of such a display produces a specific gray level at the pixel, regardless of the gray level previously present at the pixel. Furthermore, LC displays are only driven in one direction (from non-transmissive or "dark" to transmissive or "light"), the reverse transition from a lighter state to a darker one being affected by reducing or eliminating the electric field. Finally, the gray level of a pixel of an LC display is not sensitive to the polarity of the electric field, only to its magnitude, and indeed for technical reasons commercial LC displays usually reverse the polarity of the driving field at frequent intervals. In contrast, bistable electro-optic displays act, to a first approximation, as impulse transducers, so that the final state of a pixel depends not only upon the electric field applied and the time for which this field is applied, but also upon the state of the pixel prior to the application of the electric field.

Whether or not the electro-optic medium used is bistable, to obtain a high-resolution display, individual pixels of a display must be addressable without interference from adjacent pixels. One way to achieve this objective is to provide an array of non-linear elements, such as transistors or diodes, with at least one non-linear element associated with each pixel, to produce an "active matrix" display. An addressing or pixel electrode, which addresses one pixel, is connected to an appropriate voltage source through the associated non-linear element. Typically, when the non-linear element is a transistor, the pixel electrode is connected to the drain of the transistor, and this arrangement will be assumed in the following description, although it is essentially arbitrary and the pixel electrode could be connected to the source of the transistor. Conventionally, in high resolution arrays, the pixels are arranged in a two-dimensional array of rows and columns, such that any specific pixel is uniquely defined by the intersection of one specified row and one specified column. The sources of all the transistors in each column are connected to a single column electrode, while the gates of all the transistors in each row are connected to a single row electrode; again the assignment of sources to rows and gates to columns is conventional but essentially arbitrary, and could be reversed if desired. The row electrodes are connected to a row driver, which essentially ensures that at any given moment only one row is selected, i.e., that there is applied to the selected row electrode a voltage such as to ensure that all the transistors in the selected row are conductive, while there is applied to all other rows a voltage such as to ensure that all the transistors in these non-selected rows remain non-conductive. The column electrodes are connected to column drivers, which place upon the various column electrodes voltages selected to drive the pixels in the selected row to their desired optical states. (The aforementioned voltages are relative to a common front electrode which is conventionally provided on the opposed side of the electro-optic medium from the non-linear array and extends across the whole display.) After a pre-selected interval known as the "line address time" the selected row is deselected, the next row is selected, and the voltages on the column drivers are changed so that the next line of the display is written. This process is repeated so that the entire display is written in a row-by-row manner.

The invention includes a polymer composition comprising a urethane acrylate, an adhesion promoter, and a conductive monomer. Conductive monomers are typically low molecular weight (<1000 g/mol), monofunctional monomers that bring high ionic conductivity character to the cured film. In some embodiments, the monomers include polar functional groups and exhibit a moderate affinity toward water. The conductive character of a monomer (or formulation) is determined by exposing the cured film, e.g., a "homopolymer," to 25° C. and 50% relative humidity (RH) for one week and then making a measurement of the volume resistivity of the cured film. Conductive monomers typically exhibit volume resistivities of less than $10^{10}$ Ohm·cm, more typically between $1\times10^{8}$ and $9\times10^{9}$ Ohm·cm.

In addition to conductive monomers, formulations of the invention may also include nonconductive diluting monomers, cross linkers, photoinitiators, and plasticizers, among other ingredients. Like conductive monomers, non-conductive monomers are typically low molecular weight (<1000 g/mol), monofunctional monomers. However, unlike conductive monomers, nonconductive diluting monomers have measured conductivities above $10^{11}$ Ohm·cm, e.g., above $10^{12}$ Ohm·cm. Table 1 lists additives that may be added to the polymer formulation to influence the glass transition temperature ($T_g$), index of refraction, and conductivity.

TABLE 1

Glass transition temperature (Tg), index of refraction (nN), and specific gravity of monomers that can be added to formulations of the invention. A description and commercial source for each additive is listed below Table 1.

|  | SR9087 | SR339 | SR495B | SR9038 | CN966H90 | SR349 | CD9055 | CN131B | SR531 | CN3108 | CN9782 |
|---|---|---|---|---|---|---|---|---|---|---|---|
| Tg (° C.) | −24 | 5 | −53 | −42 | −35 | 67 | 70 | 13 | 10 | 25 | −32 |
| nN (RI) | 1.5038 | 1.516 | 1.4637 | 1.4933 | 1.4718 | 1.5425 | 1.4549 | 1.5247 | 1.4624 | 1.513 | 1.4900 |
| spec gravity | 1.1101 | 1.103 | 1.1 | 1.128 | 1.1 | 1.145 | 1.21 | 1.156 | 1.09 | 1.16 | 1.177 |

Sartomer SR9087 - commercially-available alkoxylated phenol acrylate monomer. Sartomer, Exton, PA.
Sartomer SR339 - commercially-available 2-phenoxyethyl acrylate monomer. Sartomer, Exton, PA.
Sartomer SR495B - commercially-available caprolactone acrylate monomer. Sartomer, Exton, PA.
Sartomer SR9038 - commercially-available ethoxylated (30) bisphenol A diacrylate monomer. Sartomer, Exton, PA.
Sartomer CN966H90 - commercially-available aliphatic polyester based urethane diacrylate oligomer blended with 10% 2(2-ethoxyethoxy) ethyl acrylate. Sartomer, Exton, PA.
Sartomer SR349 - commercially-available ethoxylated (3) bisphenol A diacrylate monomer. Sartomer, Exton, PA.
Sartomer CD9055 - commercially-available acidic acrylate adhesion promoter. Sartomer, Exton, PA.
Sartomer SR531 - commercially-available cyclic trimethylopropane formal acrylate (CTFA) monomer. Sartomer, Exton, PA.
Sartomer CN3108 - commercially-available acrylate oligomer. Sartomer, Exton, PA.
Sartomer SR256 - commercially-available acrylate oligomer. Sartomer, Exton, PA.
Sartomer CN9782 - commercially-available aromatic urethane acrylate oligomer. Sartomer, Exton PA
Sartomer CN131B - commercially-available low viscosity acrylic oligomer. Sartomer, Exton PA.

In addition to the components listed in Table 1, other additives may be included to adjust the volume resistivity, e.g., Sartomer SR440 (commercially-available isooctyl acrylate monomer) Sartomer SR395 (commercially-available isodecyl acrylate monomer), and Rahn M166 (commercially-available polyether acrylate; Rahn A G, Zurich, Switzerland). The compositions may additionally include cross-linkers such as Sartomer CN964 (commercially-available urethane diacrylate oligomer), photoinitiators, such as diphenyl(2,4,6-trimethylbenzoyl)phosphine oxide and 1-hydroxycyclohexyl-phenyl-ketone (both Sigma-Aldrich, Milwaukee, Wis.), and/or plasticizers, such as glycerol, propylene carbonate, or phthalates (available from Sigma-Aldrich). In some instances, additional adhesive resins can be added, such as Sartomer CN964 (commercially-available urethane acrylate oligomer). In some embodiments, the formulations will comprise 0 to 70% (wt/wt) conductive monomers, e.g., 5 to 50% (wt/wt), e.g., 10 to 40% (wt/wt). In some embodiments, the formulations will comprise 0 to 50% (wt/wt) nonconductive monomers, e.g., 5 to 45% (wt/wt), e.g., 10 to 40% (wt/wt). In some embodiments, the formulations will include 0 to 40% (wt/wt) cross linker, e.g., 5 to 15% (wt/wt), e.g., 10 to 15% (wt/wt). In some embodiments, the formulations will comprise 0 to 50% (wt/wt) adhesion promoters, e.g., 5 to 45% (wt/wt), e.g., 10 to 40% (wt/wt). In some embodiments, the formulations will comprise less than 2% (wt/wt) photoinitiator, e.g., about 1% (wt/wt) photoinitiator, e.g., about 0.5% (wt/wt) photoinitiator. In some embodiments, the formulations will comprise less than 2% (wt/wt) plasticizer, e.g., about 1% (wt/wt) plasticizer, e.g., about 0.5% (wt/wt) plasticizer. In some embodiments, the formulations will comprise less than 1% (wt/wt) ionic liquid, e.g., less than 0.5% (wt/wt) ionic liquid, e.g., less than 0.1% (wt/wt) ionic liquid.

In some embodiments, the formulations of the invention are substantially solventless, that is, they do not include solvents beyond the monomer components and additives themselves. For example, the formulations do not include ketones, ethers, hexanes, or other low-chain length alkane solvents without polymerizable functionality, i.e., acrylates or epoxides. Such formulations improve the reliability of layered electro-optic assemblies and other materials, i.e., VT windows, because there is less evaporative shrinking during the cure, leading to more consistent films. Furthermore, the fabrication process, itself, requires less air-handling/scrubbing and produces less organic waste.

In some embodiments, the formulations of the invention are substantially free of metals, i.e., conductive metal particles. Because the formulations do not include metal particles, there is less risk of these dense additives settling out of an adhesive suspension as the formulation is curing, which could result in an adhesive/planarizing layer with different zones of conductivity. Additionally, metal particles can adversely affect the index of refraction and cause visual defects in a finished display.

Typically, the formulations will require low viscosity (less than 5000 cP, e.g., less than 2000 cP, e.g., less than 1000 cP) to flow properly during processing, e.g., coating and lamination. Low viscosity allows the formulations to coat materials at low coat weights, yet still achieve leveling before curing. Nonetheless, the formulations must still have high enough viscosity that they do not dewet the material prior to cure, or favorably wet the ink surface. For this reason, formulations of the invention typically also include cross-linkers that are activated during curing, e.g., via photoinitiation. The type of cross-linker used may vary with the material to be coated, e.g., different cross linkers may be used depending upon whether the electro-optic medium is an encapsulated liquid polymer or an electro-optic inorganic solid. Additionally, the timing of the cross-linking during the fabrication process may vary depending upon the needs of the application. For example, in some embodiments, the adhesive layer will be cross-linked after it has been applied to the electro-optic medium or during lamination process. In other embodiments, the adhesive layer will be cross-linked after an electro-optic assembly, such as a front plane laminate, has been fabricated. When the cross-linking is initiated after fabrication, the electrode or release sheet adjacent the adhesive layer must be substantially transparent to the light needed for photoinitiation. Of course, other means for cross-linking the polymers, such as heat, can be used, depending upon the application.

The adhesion of the formulation, and the performance as a coating, can be promoted in two major ways. The first is to increase the affinity of the adhesive layer for the surfaces to be bonded. The second is to dissipate peeling forces into polymer motion instead of delamination. Importantly, if the cohesive forces among the polymer are stronger than the adhesive forces between the polymer and the surface, the polymer will be ripped from the surface. In the converse situation, i.e., the adhesive force is stronger than the cohesive force, the polymer will tear apart, leaving bits attached to the surface. For best performance, the adhesive forces are selected to be stronger than the cohesive forces amongst the polymer, however, both adhesion and cohesion should be relatively high.

Both the adhesive and the cohesive forces can be altered by modifying the functional groups of the polymer(s), as well as the length of the monomer units. For example, urethanes have a relatively strong affinity for a large variety of surfaces, but the addition of certain functional groups (e.g., carboxylic acids, amines, acetals, phenyl groups) can greatly improve adhesion, depending upon the composition of the surface. At the same time, the dissipation of energy necessary to avoid delamination when the formulation is exposed to peeling forces is improved by creating relatively long and tangled polymer chains. This can be done by using prepolymers (e.g., difunctional acrylates that are several thousand molecular weight units before curing), varying crosslinking density, or varying cure conditions.

Beyond the composition of the monomers, themselves, the refractive index of a polymer mixture can be altered with the inclusion of additives. For example, shorter and higher functionality cross linkers lead to a larger increase in refractive index, while very long cross linkers lead to small increases. Additionally, cured films typically have a slightly higher index than the uncured mixture. (The index dependence with curing is likely due to decreasing free volume in the polymer as it cures.) The refractive index of the electro-optic medium can vary substantially, for example a polymer dispersed electrophoretic medium may have a refractive index of about 1.5, while the refractive index of an electrochromic medium may be greater than 2. Once the electrophoretic medium is selected, it is possible to modify the polymer mixture of the invention, as needed, to achieve an index-matched formulation. In particular, to achieve good transparency, the index of refraction of the formulation should be as close as possible to the index of refraction of the electro-optic medium when the electro-optic medium is in a clear state.

The refractive index of the adhesive layer(s) can be tuned by the addition of high refractive metal oxide nanoparticles. Doping the adhesive with nanoparticles allows the refractive index to be tuned without impacting the Tg and conductivity. Preferred fillers have a high refractive index nanomaterial and are dispersible in a low Tg, high conductivity UV fluid continuous phase. Such compositions will leave highly conductive paths through the matrix and produce a refractive index that is the average of the nanomaterial and the cured UV fluid (so long as the filler is below the percolation concentration). Metal nanoparticles can also be included in compositions of the invention to modify the refractive index. When chosen appropriately, the composition, size, and amount of nanoparticles can alter the index of refraction of a composition so that the index of refraction of the composition matches the index of refraction of the electro-optic medium or counteracts the index of refraction of the electro-optic medium. That is, compositions of the invention can be used to tune interfaces between layers, e.g., electro-optic layers and light-transmissive electrode layers, to improve overall transmission and to reduce waviness, speckle, or other distortions. In some embodiments, the metal nanoparticles are metal oxide nanoparticles, such as zirconia nanoparticles. Suitable nanoparticles are commercially available from a number of suppliers such as Pixelligent (Baltimore, Md.) and Sigma Aldrich (Milwaukee, Wis.). The nanoparticles are typically (on average) less than 500 nm in size, for example (on average) less than 300 nm in size, for example (on average) less than 200 nm in size, for example (on average) less than 100 nm in size, for example (on average) less than 50 nm in size, for example (on average) less than 20 nm in size. In some embodiments, the nanoparticles have an average size of about 5 nm with a narrow size distribution (i.e., 3-7 nm). Additionally, the nanoparticles can be surface treated to improve dispersion and also to provide active sites for crosslinking within a polymer mixture. A variety of metal nanoparticles may be used with the invention, including zirconium, titanium, copper, indium, zinc, nickel, tin, lanthanum, and cerium nanoparticles, both surface treated and untreated. In other embodiments, oxides, carbides, or nitrides of these metals may be used to make suitable nanoparticles, for example $ZrO_2$, $TiO_2$, ZnO, MnO, NiO, CdO, $Cr_2O_3$, $Mn_2O_3$, $Fe_2O_3$, or $CeO_2$. In some embodiments, the adhesive composition comprises between 0.01% and 25% metal oxide particles (wt. particles/wt. composition). In some embodiments, the adhesive composition comprises less than 1% metal.

In addition to modifying the index of refraction and adhesive properties, the performance of a polymer formulation can be improved by modifying the conductivity. For example, in many applications involving electro-optic materials it is beneficial to have a volume resistivity on the order of $1\times10^9$ Ohm·cm. This is a relatively low volume resistivity as compared to conventional adhesives, which have volume resistivities on the order of $1\times10^{13}$ Ohm·cm (i.e., insulating). Thus, it is beneficial to select a monomer type and functionality to achieve the desired resistivity. In many cases, however, additives that increase the conductivity negatively impact the optical or mechanical properties of the formulation. For example, adding conducting metal particles greatly changes the adhesive and optical properties. Accordingly, it is necessary to make compromises in the design of the adhesive to facilitate conductivity while maintaining acceptable physical properties.

In polymeric formulations of the invention, the conductive properties are improved by adding monomers that facilitate ion transport through the cured network. There are two major ways to promote both high numbers of charge carriers and a high number of binding sites for those charge carriers. The first is to incorporate polar, rubbery, hygroscopic monomers, such as monomers including carbonyl or alkoxy groups. The second is to add organic ionic dopants. Both the polar groups and dopant clusters act as low energy sites for charge carriers, probably hydronium ions and hydroxide ions. The inclusion of conductive monomers or ionic liquids (ILs) is not exclusive, however, and in some instances, the combination may result in synergies, such as achieving a bulk volume resistivity that is lower than the additive sum of the contributions from the conductive monomers and ILs.

Ionic liquids suitable for use with the invention include organic compounds with highly charged components that are solvated by neighboring molecules, such as imidazoliums coupled to strong counter-ions, such as phosphates, sulfonamides, borates, and cyanamides. For example, 1-butyl-3-methylimidazolium hexafluorophosphate (BMIPF6), 1-butyl-3-methylimidazolium bis[(trifluoromethyl)sulfonyl]imide (BMITFSI), 1-decyl-3-methylimidazolium hexafluorophosphate (DMIPF6), 1-ethyl-3-methylimidazolium tetrafluoroborate (EMIBF4), 1-ethyl-3-methylimidazolium dicyanamide (EMIDCN), and 1-ethyl-3-methylimidazolium bis[(trifluoromethyl)sulfonyl]imide (EMITFSI).

A polymer's ability to transport solvated ions is typically quite temperature dependent, and it conductivity falls off greatly below the transition glass temperature ($T_g$) of the polymer. [The glass transition temperature is the temperature at which an amorphous solid changes between a rubber and glassy state.] Because $T_g$ is a standard measurement (Dynamic Scanning calorimetry (DSC)), the $T_g$ of a homopolymer or oligomer can be used to determine a temperature range over which the component will contribute the most to conductivity. On the flip side, if desired, a component can be chosen with a $T_g$ that falls within the operating temperature range of the device so that the polymer formulation will have markedly different conductivity at different points within the range of operating temperatures. Such a polymer may be used to create a dual stimulus electro-optic display that responds to both temperature and electrical stimulation. A dual stimulus formulation may include, for example, approximately 40% (wt/wt) hygroscopic acrylate monomer (improves conductivity, e.g., SR9088, or SR9087), approximately 10% (wt/wt) urethane acrylate oligomers (improves mechanical properties, e.g., CN964) and about 50% (wt/wt) acrylate oligomer monomer blend (tackifier/adhesion promoter; e.g., CN3108). For example, a VT window may be designed to change from clear to silvered when the temperature rises above a given temperature, thereby helping to minimize incident light from the sun on a hot day.

Figure 3:
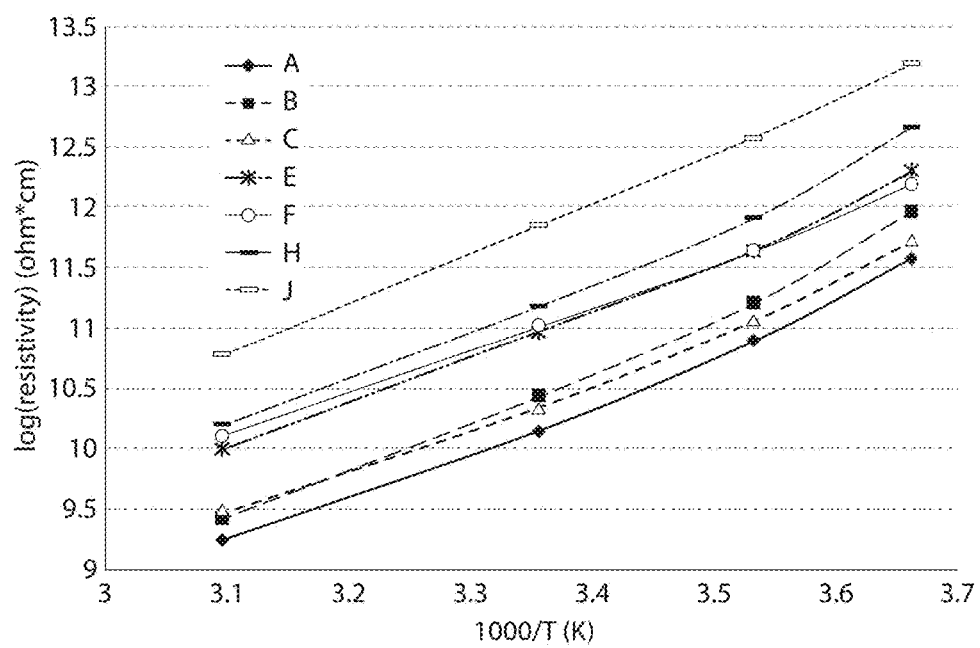
FIG. 3 shows the resistivity of various formulations of the invention as a function of temperature.

An illustration of the temperature-dependence of the conductivity of varying polymer blends is shown in FIG. 3, which plots the natural log of resistivity versus the inverse temperature multiplied by 1000. The measurements in FIG. 3 were taken with impedance spectroscopy for cured samples sandwiched between a transparent indium-tin-oxide (ITO) electrode and a carbon backplane. The compositions of formulations in FIG. 3 vary in their composition of ethylene oxide by weight. Formulations A-C each contain about 30% ethylene oxide by weight. Formulations E-H each contain about 15% ethylene oxide by weight. Formulation J contains about 8% ethylene oxide by weight.

At high temperature, i.e., the left side of the graph, all materials are significantly above their glass transition temperatures and the resistivity is at least two orders of magnitude lower than at low temperatures (right side of graph). In general, the highest conductivity will be achieved at temperatures as high above the glass transition as possible. (At arbitrarily high temperature, the polymer chain will be as free to move as it could be, however the mechanical properties may suffer.) FIG. 3 also illustrates the trend in resistivity as a function of the hygroscopic content. In particular, the top line (J) has the lowest ethylene oxide concentration and shows the highest resistivity, whereas the bottom lines (A-C) have the highest ethylene oxide concentration and show the lowest resistivity.

In practice, it is typically sufficient to operate approximately 25° C. above the glass transition temperature. Because many systems incorporating the polymer formulations will operate in a room-temperature environment, the $T_g$ of the bulk formulation should be somewhere around 0° C. or lower. As the operating temperature is generally fixed (and not arbitrarily high), this calls for purposefully creating a polymer matrix with as low a $T_g$ as possible. Of course, like the adhesive and optical properties, the glass transition temperature can also be tuned with monomer composition. In general, a mixture of monomers will produce a cured film whose $T_g$ is somewhere between the highest and lowest homopolymer $T_g$s, furthermore, the more of one monomer is added, the closer to its $T_g$ the mixture's $T_g$ will be as predicted by the Flory-Fox equation.

While the formulations are described for use in the construction of devices including electro-optic media, e.g., front plane laminates and displays, it should be appreciated that the formulations may be useful for other applications, such as conductive adhesives. For example, a formulation of the invention can be used as a conductive, pressure-sensitive adhesive. Such a formulation may include about 30% caprolactone acrylate monomer (e.g., SR495B), about 40% polyester/urethane monomer blend (e.g., CN966H90), and about 30% alkylated acrylate monomer (e.g., SR440).

Electrophoretic Display Media

Figure 2A:
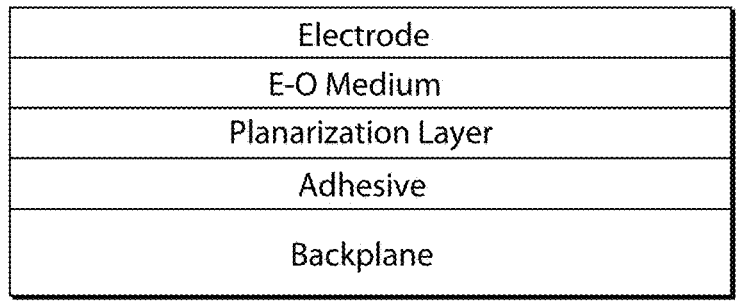
FIG. 2A illustrates a cross-section of an electro-optic display similar to that of FIG. 1A but incorporating a formulation (planarization layer) of the invention.
Figure 2B:
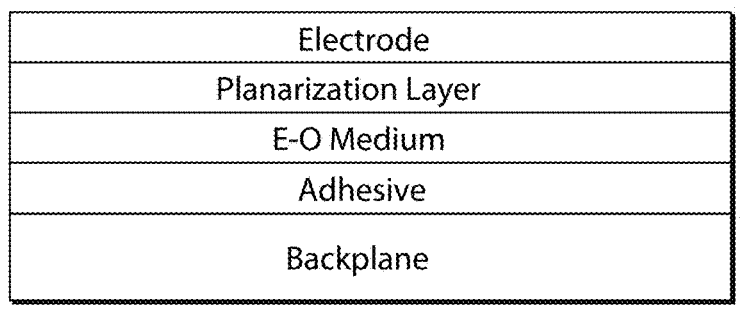
FIG. 2B illustrates a cross-section of an electro-optic display similar to that of FIG. 1B but incorporating a formulation (planarization layer) of the invention.
Figure 2C:
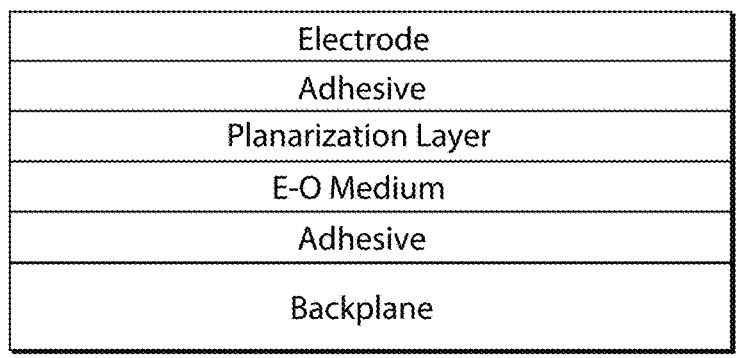
FIG. 2C illustrates a cross-section of an electro-optic display similar to that of FIG. 1C but incorporating a formulation (planarization layer) of the invention.

Formulations of the invention are well-suited for fabricating layered assemblies including electro-optic media, i.e., for use in displays, as illustrated in FIGS. 2A-2C. In particular, using the compositions and methods described above, an adhesive formula can be achieved that provides for good planarization of the electro-optic assembly, while also providing excellent adhesion between the electro-optic medium and an electrode, such as a transparent ITO electrode, or between the electro-optic medium and an adhesive layer, or between the layer of electro-optic medium and a release sheet.

In an embodiment, the formulation can be used to create a layered assembly that can be joined with a backplane to create an electro-optic display. In the embodiment shown in FIG. 4, the process begins with the deposition of a layer of electro-optic medium 310 on a layer of indium tin oxide-coated polyethylene terephthalate (PET-ITO) 320. In some embodiments, the electro-optic medium 310 may be deposited on laminate adhesive (not shown in FIG. 4) on top of the PET-ITO 320. The laminate adhesive may improve the binding between the electro-optic medium and another later-added layer, e.g., a backplane.

Figure 4:
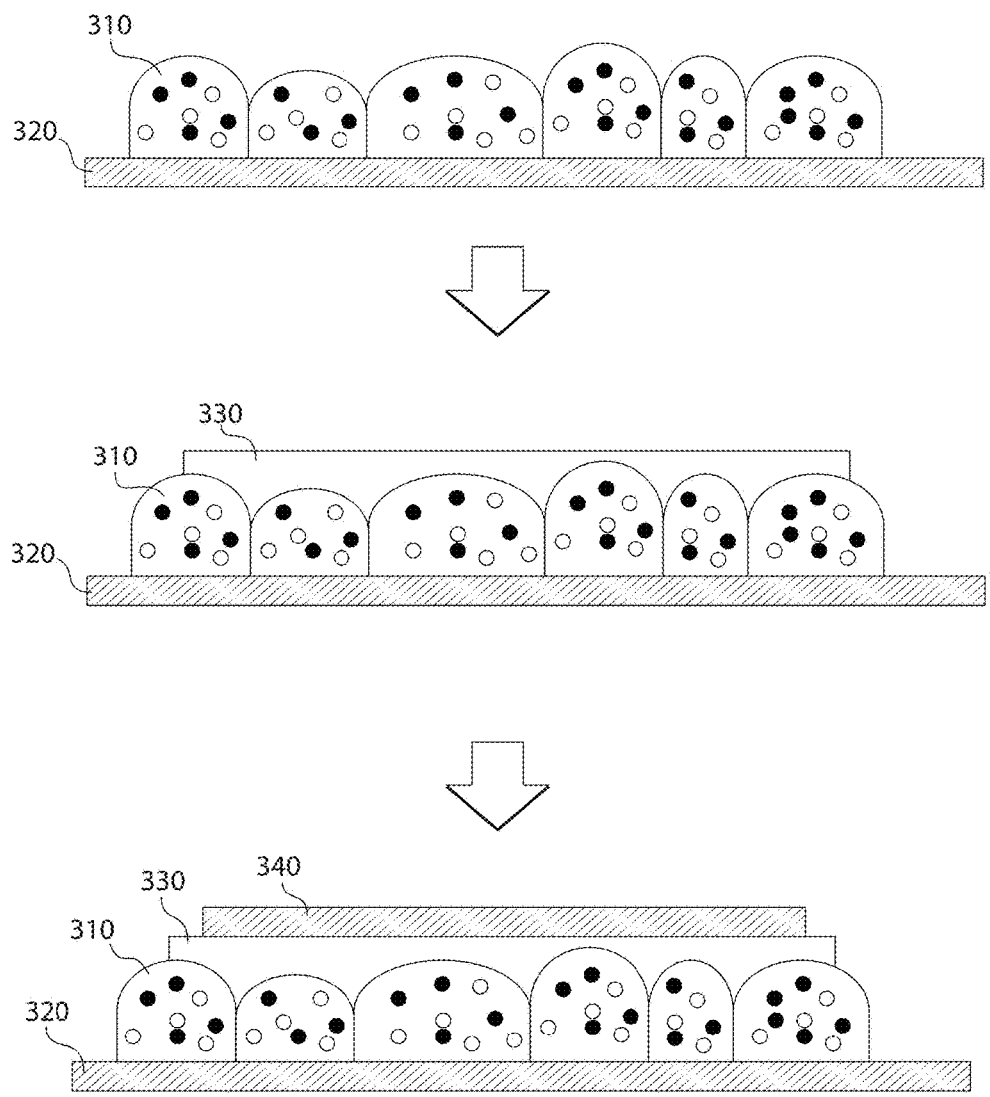
FIG. 4 illustrates the use of a formulation of the invention to improve the planarity of the electro-optic layer in an inverted front plane laminate (FPL).

After deposition on the PET ITO 320, a formulation 330 of the invention is deposited on the layer of electro-optic medium 310 to produce a substantially planar surface, i.e., as shown in the middle panel of FIG. 4. The formulation 330 may be sprayed, poured, spread, spin coated, or laminated, as discussed in greater detail below. Once the formulation 330 has been deposited on the layer of electro-optic medium 310, an adhesive layer and release sheet 340 may be adhered, laminated, etc., to the layer of formulation 330, as shown in the last panel of FIG. 4. In some embodiments, the formulation 330 is cured after it is applied to the electro-optic medium 310, but before the adhesive layer and release sheet 340 is applied. In other embodiments, the formulation 330 is cured after the adhesive layer and release sheet 340 has been applied. The curing may be with heat or photoactivation. As shown in FIG. 4, the formulation 330 results in good planarity between the adhesive layer and release sheet 340 and the PET ITO 320. As a result, when the release sheet is removed, and the electro-optic medium 310/formulation 330/PET ITO 320 is applied to a backplane, e.g., an active matrix electrode (not shown), the backplane and the PET ITO 320 will be planar across the device, resulting in consistent performance of the electro-optic medium 310. Formulations 330 of the invention allow the adhesive layer and release sheet 340 and the PET ITO 320 to be layered within 50 μm of each other in a layered assembly, e.g. less than 50 μm from each other, e.g. less than 40 μm from each other, e.g. less than 30 μm from each other, e.g. less than 25 μm from each other, e.g. less than 20 μm from each other.

The electro-optic medium 310 in FIG. 4 is depicted as an encapsulated particle system, however other electro-optic media could be used, as discussed above. Additionally, in practice, the layer of electro-optic medium 310 is much smoother than depicted in FIG. 4. (The morphology in the layer of electro-optic medium 310 has been exaggerated to illustrate the benefits of the invention.)

In some embodiments (not shown in FIG. 4), an additional adhesive layer, different from the layer of formulation 330, is added between the electro-optic medium 310 and the PET ITO 320. The extra adhesive layer can be combined with the formulation 330 to result in a hybrid planarization/adhesion layer, as described below with respect to FIG. 5B.

When the formulation 330 adheres the electro-optic medium 310 to the PET ITO 320, the resulting assembly may be referred to as an "inverted front plane laminate (FPL)," i.e., as discussed in U.S. Pat. No. 7,839,564. Such an inverted FPL may be used to form a display by removing the release sheet adjacent the electro-optic layer and laminating the remaining layers to a backplane. If the backplane is sufficiently smooth, and close attention is paid to the lamination conditions used, good, void-free lamination should be achievable, and the resulting display will show both good low temperature performance and high resolution. If void formation (i.e., areas where the electro-optic medium fails to adhere to the backplane) is found to be a problem, the release sheet adjacent the electro-optic layer can be removed from the inverted FPL and the remaining layers laminated to a thin layer of lamination adhesive previously coated on to a separate release sheet, thus forming a modified inverted FPL containing an auxiliary layer of lamination adhesive (see FIG. 2B). After removal of the release sheet covering the auxiliary adhesive layer, the modified inverted FPL can be laminated to a backplane in the same manner as previously described, with improved adhesion to the backplane. Because the surface of the electro-optic layer exposed by removal of the release sheet will be very smooth (since the electro-optic layer was coated on a smooth support), a very thin auxiliary layer (in some cases as little as 1 μm or less) of lamination adhesive will suffice in most cases. This small thickness of adhesive will not be sufficient to affect either the electro-optic performance or the resolution of the display. The conductivity of the auxiliary lamination adhesive layer can be varied, if desired, using the techniques and formulations described herein. The thicker this auxiliary layer is, the less conductive it can be, but if it is very thin (about 1 to 10 μm) it can be substantially more conductive than the planarization layer without compromising the performance improvements provided by the present invention.

As discussed previously, the layered constructions described above allow for precise control of the conductivity between the PET ITO 320 and the backplane that will be applied to the layered assembly. In some instances, a single device may require different electro-optic media 310, i.e., having different conductivity, for different portions of the device. In order to achieve a common conductivity between the electrode 340 and the backplane across the device, the different portions may each have a formulation 330 with a different conductivity to balance the differences in the conductivity of the electro-optic media 310. In other embodiments, a common electro-optic media 310 may be used for the creation of a layered assembly, however, the operating conditions, e.g., outdoors or at low temperatures, may require a different total conductivity between the electrode 340 and the backplane for optimal performance Using the techniques described herein, the conductivity of the formulation 330 can be adjusted to achieve the needed conductivity. Of course, other properties of the formulation 330 can be adjusted as needed, using the techniques described herein, for example the adhesive force, or the index of refraction, of the formulation 330 can be adjusted by modifying the formulation 330.

For certain applications, it may be advantageous to have a completely symmetrical structure, with an equally thick formulation layer 330 on either side of the electro-optic medium 310. This structure should have an effectively identical symmetrical electrical response, which might be expected to reduce or eliminate certain kinds of electro-optical artifacts. Such a display structure may be produced using a symmetrical double release film, e.g., as described in U.S. Pat. No. 7,561,324.

In yet another embodiment, the PET ITO 320 of FIG. 4 can be substituted with a second release sheet, thereby providing a structure (in effect, a modified double release film) comprising, in order, an adhesive layer release sheet 340, an electro-optic medium 310, a formulation layer 330 and a second release sheet. In such embodiments, it is possible to remove either release sheet from this modified double release film as a matter of choice. The modified double release film is effectively the equivalent of a free-standing electro-optic layer, which can be used to construct devices in several ways, for example, as described in U.S. Pat. No. 7,110,164.

Figure 5A:
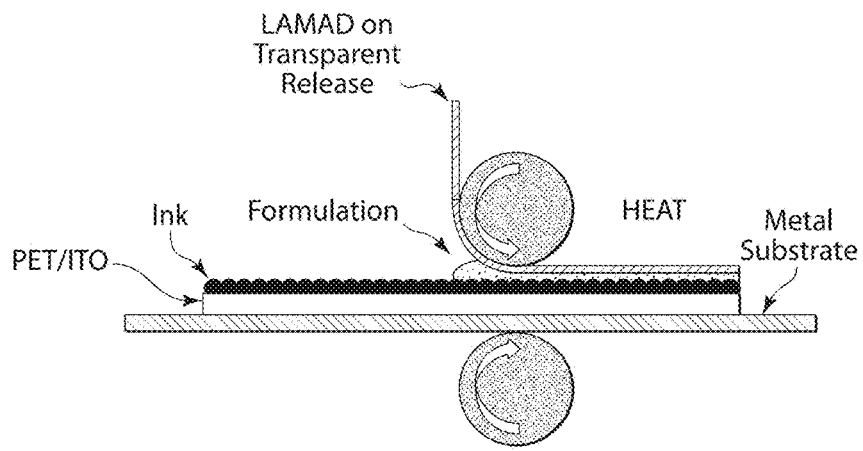
FIG. 5A depicts the use of a formulation of the invention in the creation of an FPL.
Figure 5B:
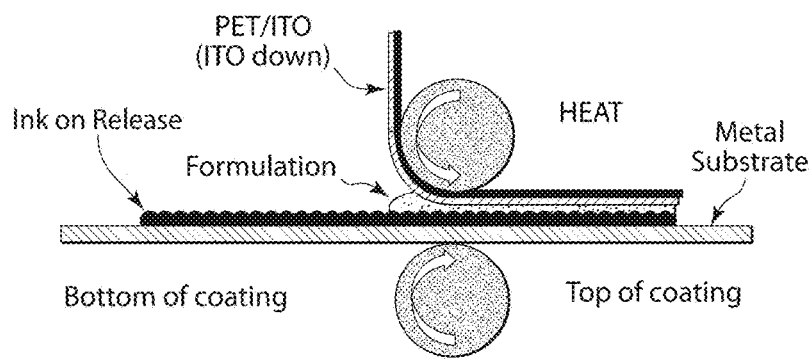
FIG. 5B depicts an alternate use of a formulation of the invention in the creation of an inverted front plane laminate.
Figure 5C:
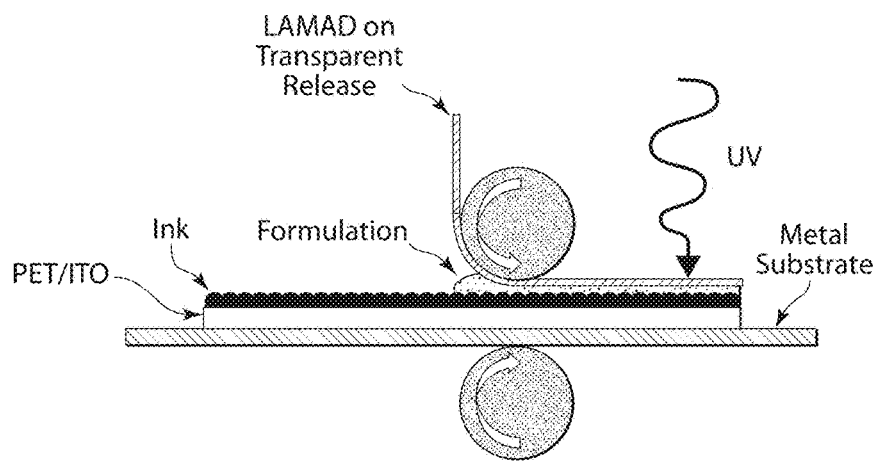
FIG. 5C depicts the use of a formulation of the invention in the creation of an FPL.

A front plane laminate (FPL) or an inverted front plane laminate (iFPL), including a formulation of the invention, may be formed with a lamination process, e.g., as shown in FIGS. 5A-5C. FIGS. 5A (FPL) and 5B (iFPL) differ from FIG. 5C in that the formulation in FIGS. 5A and 5B is heat-cured, while the formulation FIG. 5C is UV cured. A front plane laminate (FPL) can be formed by adhering the electro-optic layer ("Ink") directly to the PET/ITO electrode, applying a formulation, i.e., planarizing adhesive layer, to the electro-optic medium 310, and then applying a lamination adhesive with a release sheet to the planarizing adhesive layer. In some embodiments, the adhesive layer may interact with the planarization layer to produce a hybrid planarization/adhesive layer. An exemplary technique for completing this assembly with lamination is shown in FIG. 5A. In some embodiments, the release sheet is formed from a UV transparent material, thus allowing the formulation 330 to be cured after it has been laminated to the electro-optic medium 310, as in FIG. 5C. In some embodiments, UV curing will initiate cross-linking between the planarization and adhesive layers, thus resulting in a better bond between the electro-optic medium 310 and the backplane in the final display assembly.

Alternatively, as shown in FIG. 5B, the formulation can be deposited on the electro-optic medium atop a release, and a PET/ITO electrode 340 is then laminated atop the formulation and electro-optic medium by rolling the layers through lamination rollers, resulting in an inverted FPL structure. (While FIGS. 5A, 5B, and 5C show the use of a metal substrate, it is understood that other materials can be used for a substrate, for example flexible materials, such as polymers.) In some embodiments, the formulation 330 will be cured after the lamination, as shown in FIGS. 5A and 5B. In other embodiments, the formulation 330 will be cured before the lamination (not shown) or during the lamination (not shown). Laminates for display assemblies of the type shown in FIGS. 2A-2C can also be created using lamination techniques similar to those shown in FIGS. 5A and 5B. In some embodiments, as described previously, a second lamination adhesive layer may be added to the planarization layer, or to the electro-optic medium, to improve the integrity of the final display assembly.

Importantly, fabrication techniques that use UV curing, such as FIG. 5C, will allow for a wider range of temperature-sensitive materials to be incorporated into the devices. For example, polymer-based leads or wires, which may be susceptible to disruption by high temperatures, may be included in a layered assembly with UV curable adhesives. Additionally, performing the lamination at or near room temperature reduces outgassing that can lead to bubbles between the layers. In embodiments where the electro-optic medium is a liquid, e.g., water-based or water-permeated, UV curing will avoid swelling and/or dehydration of the medium. In such instances, UV curing will not only reduce the rate of defects in a layered assembly, but it will reduce the amount of post-process conditioning, e.g., rehydration, required in the process.

The ability to planarize an electro-optic layer using a thin, curable formulation allows for the application of an adhesive coating of less than 25 µm, potentially as thin as 10 µm, potentially as thin as 5 µm, potentially as thin as 3 µm, without the formation of significant lamination voids. Additionally, such planarization layers can be used to create multilayered, electro-optic media, such as multi-layer encapsulated electrophoretic media. Multi-layered electro-optic material may allow simultaneous presentation of, e.g., multiple colors or multiple polarizations. In particular, the planarization formulas described herein are useful for the assembly of separately addressable layers with no interlayer contamination. In the instance of a reflective electro-optic medium, such as electrophoretic pigments, the thin planarizing layers also improve the reflectivity of the medium, leading to greater dynamic range (depth of gray scale).

In addition to the above properties, planarization layers allow the use of direct-coating to create color filter array (CFA) elements, while minimizing parallax (i.e., loss of dynamic range due to viewing angle). In an embodiment, because the upper surface electrode is very parallel to the backplane, the upper electrode can be simply coated with colored materials to create colored pixels. Alternatively, a separately-fabricated filter can be adhered to the front plane, without fear that different pixels of the same color will display different colors and/or intensity because of differences in the surface morphology.

EXAMPLE 1—Evaluation of Surface Planarity

A UV curable planarization layer including (meth)acrylated polyurethane oligomer resins was prepared for deposition on an encapsulated electrophoretic medium. The formulation was prepared by mixing 45 parts-per-hundred-resin (phr) (meth)acrylated resin (SR9088) and 15 phr polyester urethane diacrylate oligomer (CN964) and 40 phr acrylate oligomer (CN3108) in a bottle, heating the mixture to 60° C. for 2 hours, then rolling overnight, to produce a high-viscosity polymer mixture. After thorough mixing, 1 phr of 1-hydroxycyclohexyl-phenyl-ketone (CPK) photoinitiator and 1 phr of diphenyl(2,4,6-trimethylbenzoyl)phosphine oxide (TPO) photoinitiator were added, and the mixture was heated to 40° C. for 2 hours, and the formulation was rolled overnight, again, to homogenize the mixture.

The UV curing formulation described above was spread over an electro-optic medium on a release sheet using bar-coating, with the bar set for a 1 mil (25 µm) gap thickness. The coating step was followed by 1 minute of curing using a Delo 30S chamber (Delo Industrial Adhesives, Windach, Germany) with a 365 nm lamp having an output of 85 mJ/cm$^2$. After curing, the surface roughness of the coated and uncoated ink was measured by interferometry.

Figure 6:
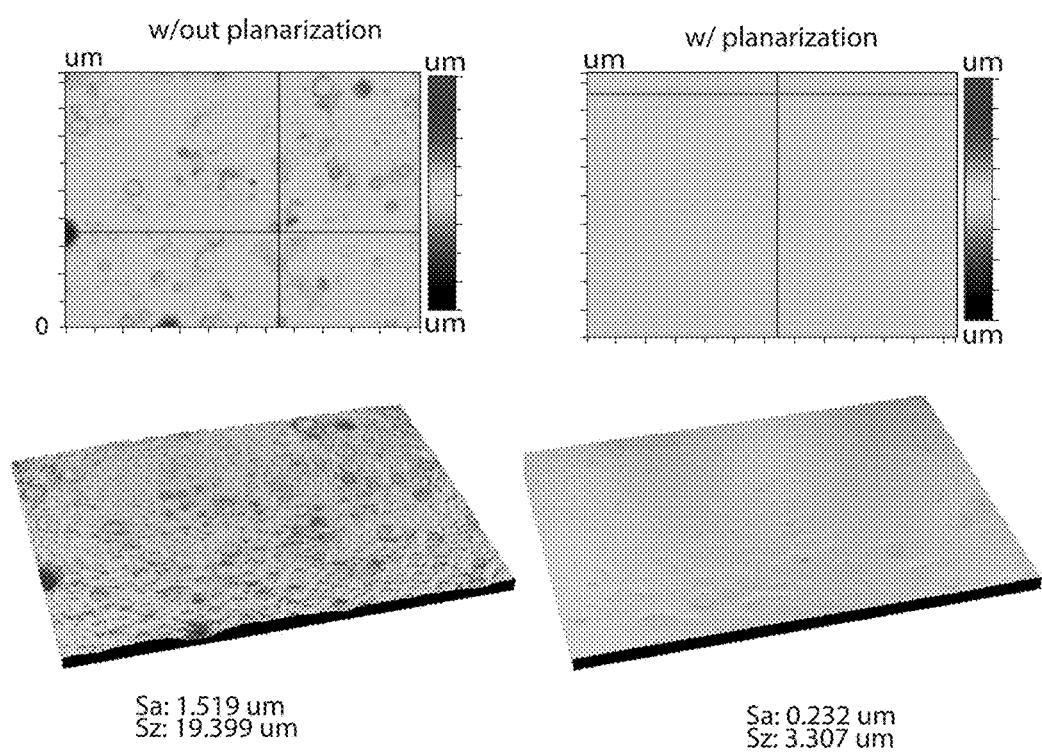
FIG. 6 contrasts surface interferometry measurements of an electro-optic medium without a formulation of the invention, and with a formulation of the invention, as a planarization layer.

Using interferometry, the surface roughness (Sa) of the uncoated electro-optic media was measured to be ~1.5 µm with a standard deviation of ~0.1 µm, while the Sa of the electro-optic media overcoated with a 15 µm UV-curable formulation was measured to be ~0.2 µm with a standard deviation of 0.04 μm. The difference between the coated and uncoated electro-optic media is easily visualized in FIGS. 6, 7A, and 7B. As shown in FIG. 6, the darker areas represent surface features above and below the median height for the sample. The sample on the left-hand side of FIG. 6 is the uncoated electro-optic medium, i.e., the sample without planarization. In contrast, the electro-optic medium was coated with the formulation in the sample on the right. Clearly, there is much less surface variation with the use of a planarization layer.

Figure 7A:
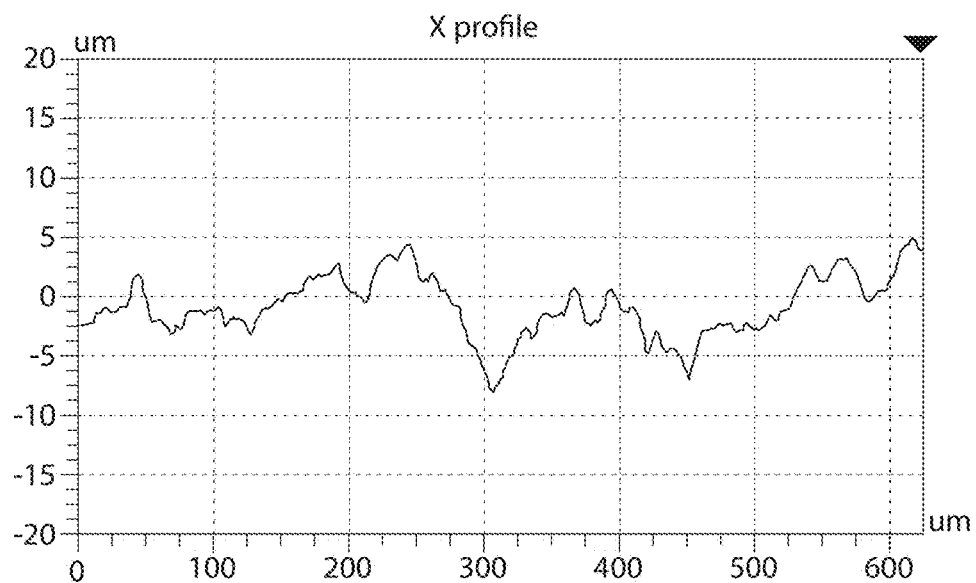
FIG. 7A shows surface morphology measurements of an electro-optic medium without a formulation of the invention as a planarization layer.
Figure 7B:
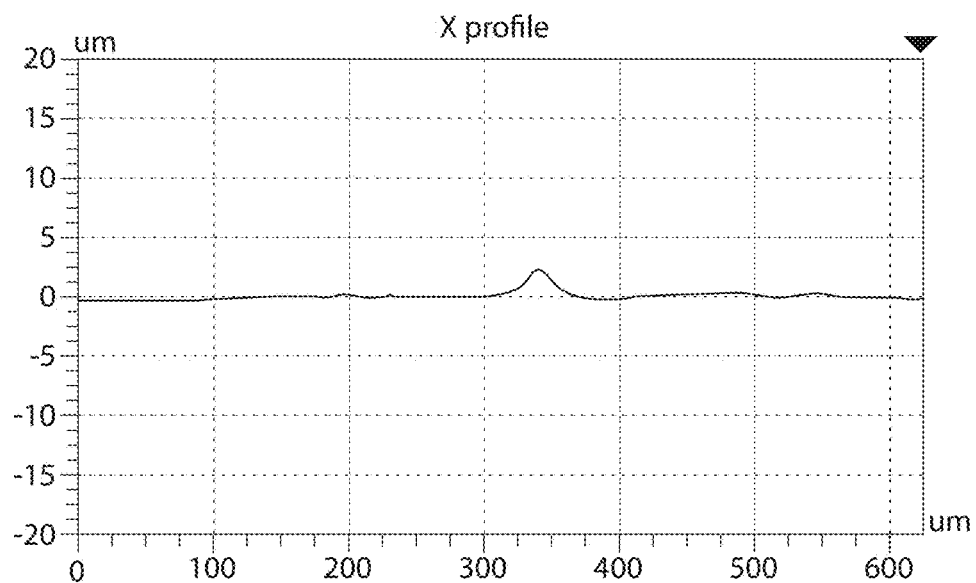
FIG. 7B shows a surface morphology measurement of an electro-optic medium with a formulation of the invention as a planarization layer.

The variations in surface morphology in FIG. 6 are easy to visualize in FIGS. 7A and 7B, where an arbitrary one-dimensional slice has been cut in the X-direction in both planar measurements of FIG. 6 to show that the planarized electro-optic medium is substantially flatter. As shown in FIG. 7A, the uncoated material has heights ranging from 5 μm to almost 10 μm, whereas the coated material (FIG. 7B) has a height at ~0 μm and an isolated peak at 3 μm. These results indicate very good planarization across the entire surface with a 15 μm coating, which will result in better electro-optic display performance. The small features shown in FIG. 7B can be eliminated by increasing the coating thickness to 30 μm, which may or may not be desirable, depending on the application.

EXAMPLE 2~Evaluating Formulation Performance

In addition to providing improved planarity between the top electrode and the backplane, the formulations also improved the stability of a four-layer structure (electrode/electro-optic medium/planarization formulation/electrode) including the formulation. Structures including the formulation did not delaminate under strains that caused a similar four-layer structure (release/electro-optic medium/conventional adhesive/electrode) to delaminate.

Four-layer structures, containing planarization formulations in the place of conventional adhesive, also demonstrated improved performance, as measured by switching speed and dynamic range. This is likely due to conventional adhesives being roughly insulating when applied at thicknesses of 5-30 μm. Addition of a UV planarization layer to a layer of encapsulated bistable (black/white) electrophoretic medium coated directly on ITO showed a speed boost to both the white and the dark states with a 250 ms pulse at 15 V, as shown in FIG. 8.

Figure 9:
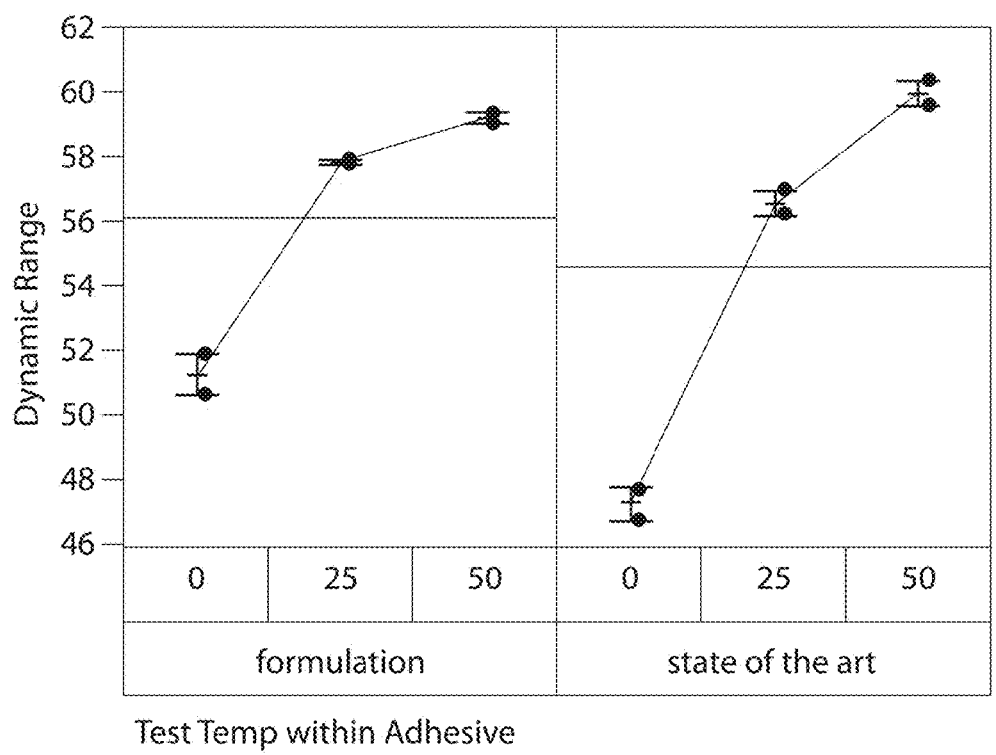
FIG. 9 shows increased dynamic range in L* at low temperatures in electro-optic displays using formulations of the invention as an adhesive layer (left), and in electro-optic displays using conventional adhesive layers.

An alternative formulation comprising 45 phr SR9087, 15 phr SR9038, 40 phr CN3108, 0.5 phr diphenyl(2,4,6-trimethylbenzoyl)phosphine oxide and 0.5 phr 1-hydroxycyclohexyl-phenyl-ketone was prepared using the techniques described above. This formulation was coated onto an encapsulated electrophoretic bistable electro-optic medium, and the coating was cured with a D-lamp and laminated to a backplane with a urethane adhesive layer then conditioned for 1 week at 50° C. and 50% RH. The dynamic range of the electrophoretic medium was then evaluated using photometry at a variety of temperatures. The results are shown in FIG. 9 as "formulation." For comparison, a conventional adhesive, used in commercially-available encapsulated electrophoretic bistable displays was prepared in the same way and tested ("state of the art" in FIG. 9). As shown in FIG. 9, the dynamic range of the formulation was better than the state of the art at 0° C. and 25° C., and only marginally worse at 50° C. However, because commercial electrophoretic medium devices are typically used in a temperature range of −10° C. to 40° C., the formulation represents a marked improvement in performance under typical operating temperatures.

Variable Transmission Media

Figure 8A:
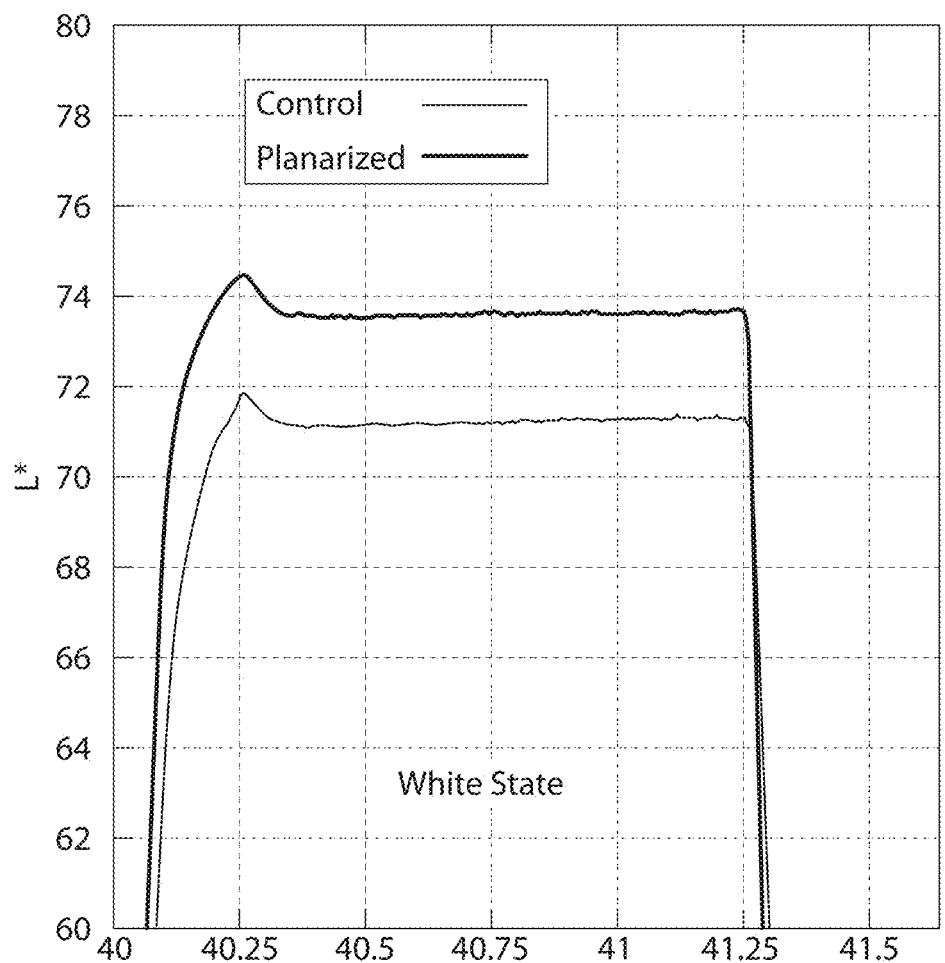
FIG. 8A compares response times to achieve a white state for an electrophoretic display using conventional adhesives (Control), and an electrophoretic display using formulations of the invention (Planarized).
Figure 8B:
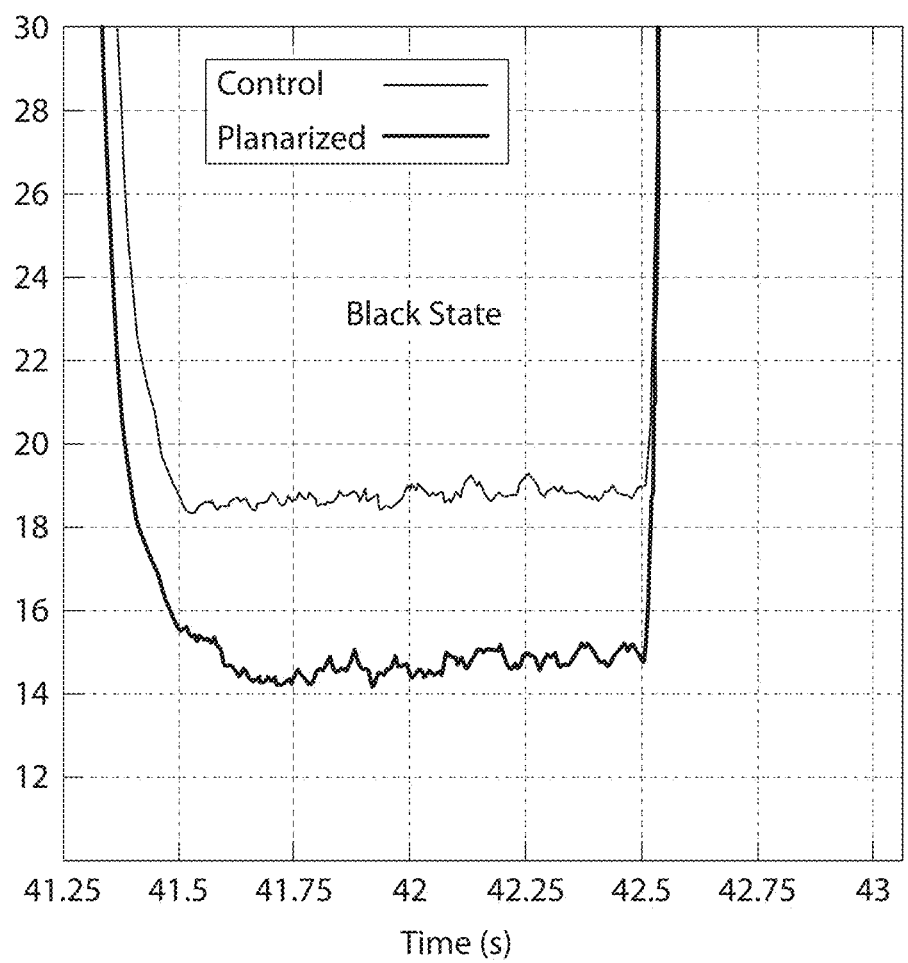
FIG. 8B compares response times to achieve a black state for an electrophoretic display using conventional adhesives (Control), and an electrophoretic display using formulations of the invention (Planarized).

The polymer formulations of the invention can additionally be used for the creation of variable transmission (VT) media, such as "smart glass," where the application of a voltage will result in a change in optical transmission of the media. In general, the structure of a VT medium is similar to that shown for an electro-optic medium, i.e., as shown in FIGS. 2A-2C. Whereas an electro-optic medium will typically include a backplane with active matrix electrodes, the VT medium includes a transparent substrate and a second transparent electrode, such as shown in FIGS. 8A and 8B. In some embodiments, the electro-optic material can be an encapsulated electrophoretic medium, in other embodiments, the electro-optic material is a polymer-dispersed electrophoretic medium, such as described in U.S. Pat. No. 6,866,760, incorporated by reference herein in its entirety. Of course, the VT media may also be constructed with alternative electro-optic materials, such as those described above, for example electrochromic materials.

EXAMPLE 3—UV Polymer Formulations for VT Glass

Figure 10A:
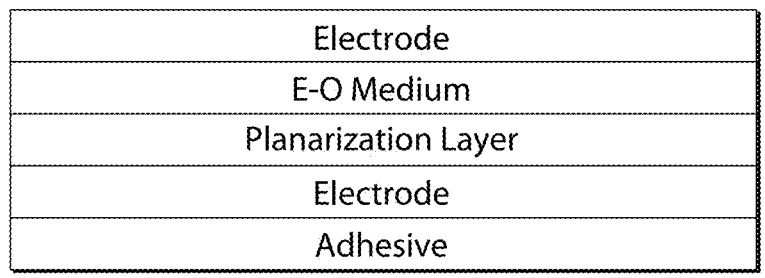
FIG. 10A shows a cross-section through an active laminate using a formulation of the invention as a planarization layer/adhesive.
Figure 10B:
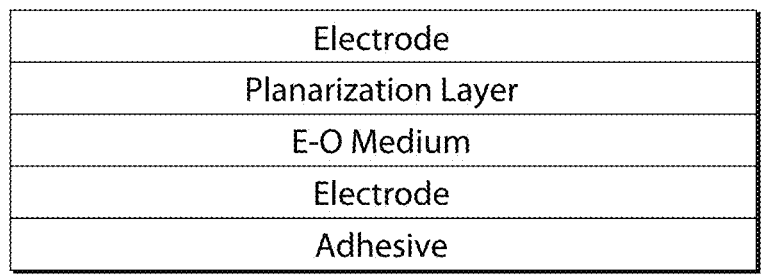
FIG. 10B shows a cross-section through an active laminate using a formulation of the invention as a planarization layer/adhesive.

Several UV-activated polymer formulations were prepared for use as adhesives and for planarizing a polymer-dispersed electrophoretic (PDEPID) layer or an encapsulated electrophoretic particle layer to be incorporated into VT glass. The formulations will be used to bond an ITO (PET/ITO front electrode) to the polyvinyl alcohol binder of a PDEPID skim coat, as depicted in FIG. 10B. While only variable transmission devices are exemplified below, a variable reflectivity device can be constructed using the same techniques, but using a reflective substrate in lieu of the transparent medium. Such a construction is shown in FIGS. 11A and 11B. Of course, switching variable transmission films that can be applied to existing substrates, e.g., windows, mirrors, signs, walls, metal, etc. In one embodiment of a variable reflectivity device, the reflective substrate is a mirror, e.g., silvered glass. In another embodiment, the reflective substrate is a material having high luster, e.g., a polished metal surface, or a colored glossy surface. The variable reflectivity devices shown in FIGS. 11A and 11B can be used to modify the luster of a surface on demand, among other applications.

Each blend of monomers was prepared by weighing out the monomers and combining the monomers noted in Table 2 in an amber vial along with photoinitiators and ionic liquids. The mixtures were then rolled for 12 hours on a roll mill to ensure even mixing of the formulations. In some instances, the monomers were warmed prior to mixing to decrease viscosity. Once completed, each formulation was evaluated for index of refraction, volume resisitivity, and maximum peel force. The surface treated zirconia nanoparticles were purchased commercially (PCPB-50 ETA and PCPG-50 ETA, Pixelligent, Baltimore, Md.) as suspended in ethyl acetate, which was removed with rotary evaporation after adding the surface treated zirconia to the solutions. Volume resistivity measurements involved curing each film between two planes of ITO glass, and then measuring the impedance with a Solartron impedance analyzer (Solartron Analytical, Farnborough, UK).

TABLE 2

Composition of polymer formulations prepared for use in VT Glass.

| Name | Composition | Index | Conduct. (S/cm) | Max peel/ft · lbs |
|---|---|---|---|---|
| NOA74 | Mercaptoester acrylate (50 phr) Isodecyl acrylate (50 phr) | 1.52 | $1 \times 10^{-13}$ | N/A |
| 929-47A | CN3108 (40 phr), SR9038 (60 phr) | 1.521 | $1 \times 10^{-9}$ | ~0 |
| 929-47E | CN3108 (59 phr), SR9038 (26 phr), SR531(15 phr) | 1.5275 | $1 \times 10^{-10}$ | 0.25 |
| 929-59D | SR339 (30 phr, SR9038 (30 phr), SR531 (29 phr), CD9055 (11 phr) | 1.519 | $6 \times 10^{-11}$ | 0.35 |
| 1097-70 | CN3108 (40 phr), SR9038 (20 phr) CN131B (40 phr) | 1.54 | $1.8 \times 10^{-11}$ | |
| 1141-81C | CN3108 (40 phr), SR9038 (20 phr), SR9087 (20 phr), CN131B (20 phr), surface treated nano ZrO$_2$ (6 phr) | 1.541 | $1.4 \times 10^{-10}$ | N/A |
| 1141-86 | CN3108 (40 phr), SR9087 (40 phr), CN131B (20 phr), surface treated nano ZrO$_2$ (12 phr) | 1.541 | $3.6 \times 10^{-10}$ | N/A |
| 1095-39 | SR9087 (45 phr), SR9038 (15 phr), CN3108 (40 phr) | N/A | $5.3 \times 10^{-10}$ | N/A |

Viewing Table 2, it is clear that the conductivity and index of refraction can be tuned by varying the composition of the formulation. Such formulations, thus, provide a variety of options for planarizing and adhering layers in variable transmission media, depending upon the operating conditions and the composition of the materials used, e.g., electro-optic medium and transparent medium.

EXAMPLE 4—Modifying Glass Transition Temperature

Figure 12:
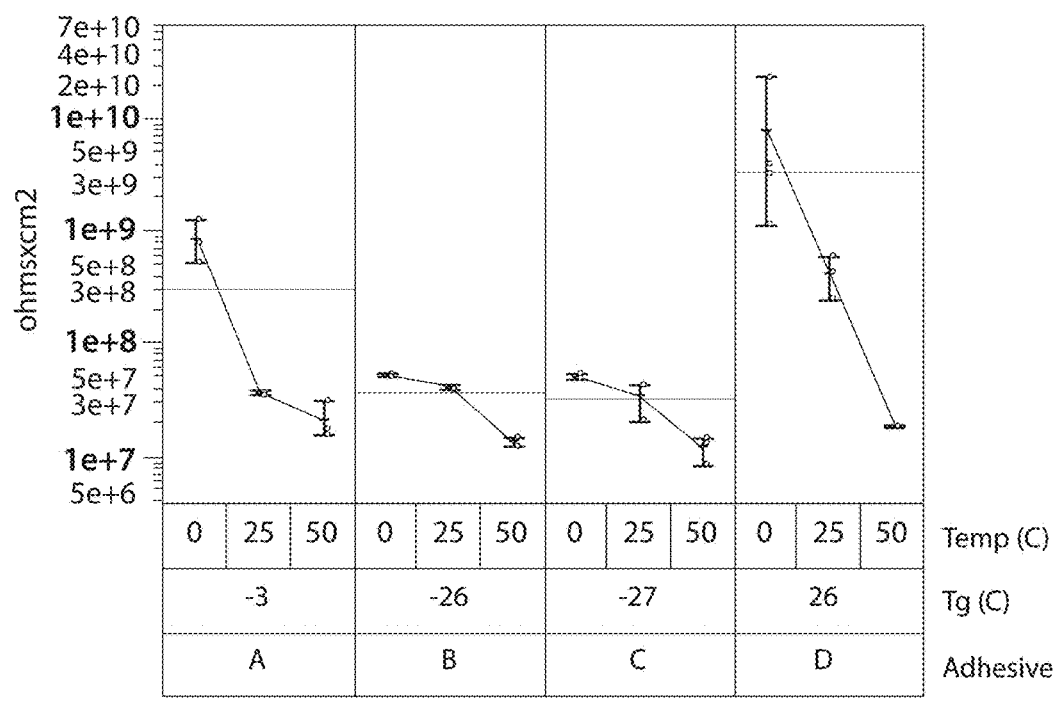
FIG. 12 shows the variation in conductivity with temperature for four exemplary compositions.

In addition to modifying the index of refraction, it is also possible to decouple the refractive index of formulations from the $T_g$ and conductivity. This can be done by adding nanoparticles that alter the index of refraction, but disperse to provide highly conductive paths through the matrix. The ability to decouple the index of refraction from the $T_g$ and the conductivity is illustrated with the formulations below, and the graphs of FIG. 12. In practice, it is desirable to keep the $T_g$ of the formulation as low as possible so that the conductivity response of the formulation to temperature will be as flat as possible. Thus, a display or VT device incorporating the formulations will be stable over a greater range of operating temperatures. Adhesive formulations are listed below. Formulation A was an organic only formulation, Formulation B included surface treated zirconia nanoparticles, Formulation C was Formulation B without surface treated zirconia nanoparticles, and Formulation D was a high $T_g$ formulation. FIG. 12 shows the resistivity of displays built with these adhesives as well as the $T_g$ of each adhesive. As is clear in comparing Formulations B and C in FIG. 12, the addition of the surface treated zirconia nanoparticles effectively flattens the conductivity curve over a range of temperatures.

Formulation A:
40 phr CN3108 urethane acrylate blend; 20 phr SR9038 ethoxylated (30) bisphenol-A diacrylate; 40 phr CN131B low viscosity acrylic oligomer; 0.5 phr TPO photo initiator; and 0.5 phr CPK photo initiator.

Formulation B:
50 phr CN3108 urethane acrylate blend; 30 phr SR495B caprolactone acrylate; 20 phr SR9038 ethoxylated (30) bisphenol-A diacrylate; 50 phr Pixclear PG 50 wt % nanozirconia sol in PGMEA (after removal of PG, 0.5 phr TPO photoinitiator, and 0.5 phr CPK photoinitiator.

Formulation C:
50 phr CN3108 urethane acrylate blend; 30 phr SR495B caprolactone acrylate; 20 phr SR9038 ethoxylated (30) bisphenol-A diacrylate; 0.5 phr TPO photoinitiator, and 0.5 phr CPK photoinitiator.

Formulation D:
15 phr SR495B, 40 phr CN3108, 45 phr SR349 ethoxylated (3) bisphenol-A diacrylate, 0.5 phr TPO photoinitiator, and 0.5 phr CPK photoinitiator Determining Thickness with X-Ray Fluorescence (XRF)

The invention additionally includes methods to measure the thickness of the adhesive and/or planarization layer described herein. The invention is in contrast to traditional coat-weight and direct thickness measurements (e.g., using calipers), which fail due to variations in the thickness and per area weights of the various other layers in transparent display. For example, while many adhesive layers have a characteristic signature in the IR, that signal is typically dwarfed and/or convoluted by the signal from the ITO or other layers in the display.

Serendipitously, many of the metal or metal oxide nanoparticles that can be added to compositions of the invention to modify the index of refraction have pronounced X-ray fluorescence signals. In particular, metal or metal oxide nanoparticles including metals with an atomic number of greater than 18 have characteristic X-ray fluorescence signatures that are easily resolved with commercial XRF methods. Using suitable evaluation equipment, such as that provided by Thermo-Fisher (Waltham, Mass.), fabricated electro-optic materials, such as displays or variable transmission films, can be evaluated for layer thickness as they are processed, during cure, or after cure, without a need to cut into the material. Techniques for evaluating materials with XRF are known, and described in textbooks, such as Skoog, Principles of Instrumental Analysis, and various patents and patent applications such as U.S. Pat. No. 5,821,001 and US 20120258305, both of which are incorporated by reference in their entireties.

EXAMPLE 5—XRF Determination of Layer Thickness

Adding metal oxide nanoparticles in the recited ranges (i.e., less than 20 phr) also allows for non-destructive quantitation of the thickness of a layer of the composition by X-Ray Fluorescence (XRF). In particular, when well-dispersed nanoparticles, with a tight distribution of sizes, are distributed in a composition there is a nearly linear relationship between XRF signal intensity and layer thickness.

Figure 13:
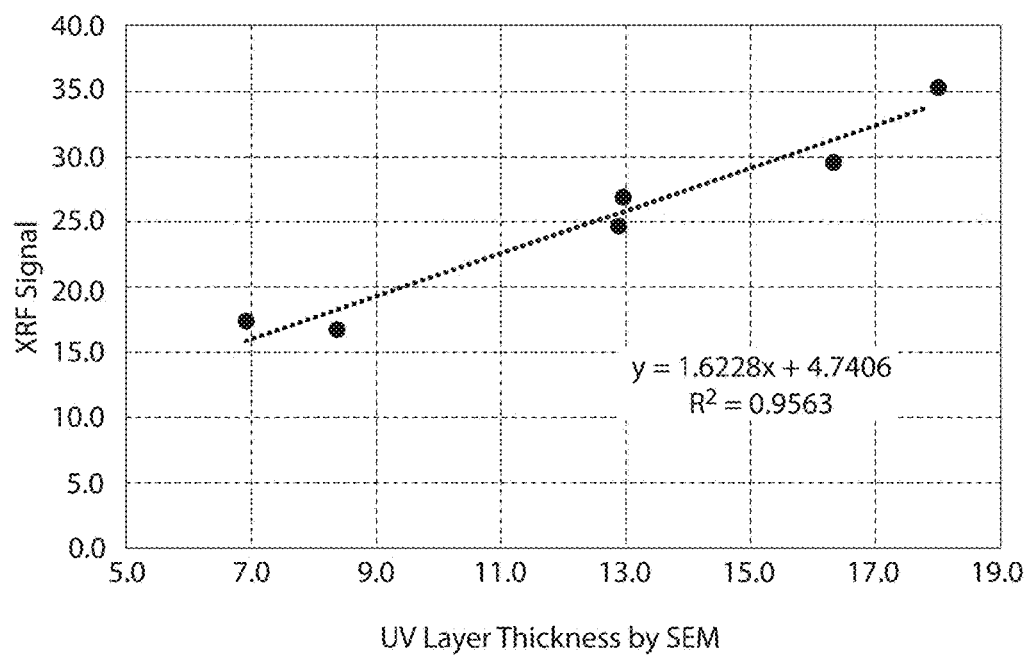
FIG. 13 shows a measured correlation between zirconia X-ray fluorescence signal intensity and the thickness of a layer comprising zirconia nanoparticles, as measured with SEM.

A series of front-plane laminates was built using the zirconia-doped Formulation B of EXAMPLE 4, above. The different laminates included different adhesive coat weights, which resulted in a series of FPLs with varying thickness adhesive layers. Each laminate part was cut, and cross-sections were analyzed with scanning electron microscopy (SEM) to measure the thickness of the layers including the metal oxide nanoparticles. After measurement with SEM, the layers were evaluated with X-ray fluorescence spectroscopy using a Spectro-XEPOS XRF spectrometer (Spectro Analytical Instruments, Kleve, Germany) A plot of Zr signal by XRF versus coat weight by SEMs is shown in FIG. 13. The relationship between measured thickness and XRF signal is nearly linear over a typical range of adhesive thicknesses (i.e., 5-20 μm). Thus, for the formulation described, the Zr XRF signal can be used calculate the adhesive thickness.

Importantly, Zr XRF measurements can be done independently of the presence of electro-optic material, light-transmissive electrode, or secondary adhesive layers. Furthermore, there is no need to switch the electro-optic state to one state or another, so the same XRF equipment can be used to evaluate laminate layer thickness whether the front-plan laminate is being produced for use in a display or a variable transmission film. Because XRF is able to determine concentrations of a large range of elements, the same approach could be pursued with any of a number metal of oxide nanoparticles, including zirconia, titania, zinc oxide, chromium oxide, iron oxide, etc. In some embodiments, it may be desired to have multiple adhesive layers with different nanoparticles comprising different metals so that separate XRF signals can be used to evaluate the thickness of multiple different layers.

It will be apparent to those skilled in the art that numerous changes and modifications can be made in the specific embodiments of the invention described above without departing from the scope of the invention. Accordingly, the whole of the foregoing description is to be interpreted in an illustrative and not in a limitative sense.

The invention claimed is:

1. A conductive adhesive composition comprising:
   a urethane acrylate;
   an adhesion promoter;
   a conductive monomer comprising alkoxylated acrylate;
   an ionic liquid comprising a phosphate, a borate, a sulfonamide, or a cyanamide;
   and, wherein the composition has a volume resistivity from $10^6$ to $10^{10}$ Ohm·cm after being conditioned for one week at 25° C. and 50% relative humidity.

2. The composition of claim 1, wherein the ionic liquid is present at less than 0.1 wt. % of the ionic liquid/wt. % of the composition.

3. The composition of claim 1, further comprising a photoinitator.

4. The composition of claim 1, further comprising cross-linkers.

5. The composition of claim 1, further comprising metal oxide particles.

6. The composition of claim 5, wherein the metal oxide particles have an average particle size of 100 nm or less.

7. The composition of claim 5, wherein the metal oxide particles comprise a metal with an atomic number greater than 18.

8. The composition of claim 7, wherein the metal is selected from the group consisting of titanium, copper, indium, zinc, nickel, tin, lanthanum, cerium, and zirconium.

9. The composition of claim 5, wherein the composition comprises between 0.01 wt. % and 25 wt. % of the metal oxide particles/wt. % of the composition.

10. The composition of claim 1, wherein the composition contains less than 1% metal.

11. The composition of claim 1, wherein the molecular weight of the conductive monomer is less than 1000 g/mol.

12. The composition of claim 1, further comprising a nonconductive monomer that has a volume resistivity of greater than $10^{10}$ Ohm·cm when cured as a homopolymer.

13. The composition of claim 1, wherein the composition has an index of refraction of 1.0 to 2.0 for visible light.

14. An active material comprising:
    an electro-optic medium;
    a light-transmissive electrode; and
    the conductive adhesive composition of claim 1.

15. The active material of claim 14, further comprising a second light-transmissive electrode.

16. A method for fabricating an electro-optic display comprising:
    providing an electro-optic medium;
    contacting the electro-optic medium with the conductive adhesive composition of claim 1; and
    curing a coating, thereby creating a smooth surface.

* * * * *